United States Patent
Carrick et al.

(10) Patent No.: US 8,999,675 B2
(45) Date of Patent: Apr. 7, 2015

(54) DENGUE VIRUS ASSAY

(75) Inventors: James M. Carrick, San Diego, CA (US); Jeffrey M. Linnen, Poway, CA (US)

(73) Assignee: Gen-Probe Incorporated, San Diego, CA (US)

(*) Notice: Subject to any disclaimer, the term of this patent is extended or adjusted under 35 U.S.C. 154(b) by 549 days.

(21) Appl. No.: 12/873,231

(22) Filed: Aug. 31, 2010

(65) Prior Publication Data

US 2011/0081646 A1 Apr. 7, 2011

Related U.S. Application Data

(60) Provisional application No. 61/238,637, filed on Aug. 31, 2009.

(51) Int. Cl.
 *C12P 19/34* (2006.01)
 *C12Q 1/70* (2006.01)

(52) U.S. Cl.
 CPC ..................... *C12Q 1/701* (2013.01)

(58) Field of Classification Search
 None
 See application file for complete search history.

(56) References Cited

U.S. PATENT DOCUMENTS

| | | | |
|---|---|---|---|
| 5,283,174 A | 2/1994 | Arnold, Jr. et al. | |
| 5,399,491 A | 3/1995 | Kacian et al. | |
| 5,744,140 A | 4/1998 | Paoletti et al. | |
| 5,744,141 A | 4/1998 | Paoletti et al. | |
| 6,136,561 A | 10/2000 | Ivy et al. | |
| 6,165,477 A | 12/2000 | Ivy et al. | |
| 6,184,024 B1 | 2/2001 | Lai et al. | |
| 6,455,509 B1 | 9/2002 | Kochel et al. | |
| 6,497,884 B1 | 12/2002 | Pletnev et al. | |
| 6,660,273 B2 | 12/2003 | Pletnev et al. | |
| 6,676,936 B1 | 1/2004 | Lai et al. | |
| 6,749,857 B1 | 6/2004 | Peters et al. | |
| 6,855,521 B2 | 2/2005 | Callahan et al. | |
| 7,041,255 B2 | 5/2006 | Wang | |
| 7,052,878 B1 | 5/2006 | Callahan et al. | |
| 7,094,411 B2 | 8/2006 | Kinney et al. | |
| 7,226,602 B2 | 6/2007 | Whitehead et al. | |
| 7,312,036 B2 | 12/2007 | Sampath et al. | |
| 7,351,547 B2 | 4/2008 | Wong et al. | |
| 7,355,033 B2 | 4/2008 | Shi et al. | |
| 7,384,785 B2 | 6/2008 | Wong et al. | |
| 7,390,495 B2 | 6/2008 | Despres et al. | |
| 7,416,840 B2 | 8/2008 | Zhu et al. | |
| 7,459,163 B2 | 12/2008 | Yamshchikov | |
| 7,468,418 B2 | 12/2008 | Iversen et al. | |
| 7,482,017 B2 | 1/2009 | Barrett et al. | |

(Continued)

FOREIGN PATENT DOCUMENTS

| | | |
|---|---|---|
| EP | 0872553 A1 | 10/1996 |
| EP | 1018556 A1 | 12/2000 |

(Continued)

OTHER PUBLICATIONS

Wu et al. (2001) J. Clinical Microbiol. vol. 39 No. 8 pp. 2794-2798.*

(Continued)

*Primary Examiner* — Suchira Pande
(74) *Attorney, Agent, or Firm* — Charles B. Cappellari; Michael J. Gilly

(57) ABSTRACT

Nucleic acid assays for detecting nucleic acids of Dengue virus serotypes 1-4 derived from 5' NTR.

12 Claims, 3 Drawing Sheets

(56) References Cited

U.S. PATENT DOCUMENTS

| | | | |
|---|---|---|---|
| 7,507,415 B2 | 3/2009 | Arroyo et al. |
| 7,517,531 B2 | 4/2009 | Whitehead et al. |
| 7,524,508 B2 | 4/2009 | Pang et al. |
| 7,560,118 B2 | 7/2009 | Whitehead et al. |
| 7,641,907 B2 | 1/2010 | Kinney et al. |
| 7,641,908 B2 | 1/2010 | Kinney et al. |
| 7,641,909 B2 | 1/2010 | Kinney et al. |
| 7,718,357 B2 | 5/2010 | Guy et al. |
| 7,718,358 B2 | 5/2010 | Guy et al. |
| 7,718,359 B2 | 5/2010 | Guy et al. |
| 7,749,734 B2 | 7/2010 | Kouichi et al. |
| 7,790,173 B2 | 9/2010 | Lazo Vazquez et al. |
| 7,790,452 B1 | 9/2010 | Sagripanti et al. |
| 7,807,801 B2 | 10/2010 | Iversen et al. |
| 7,811,579 B2 | 10/2010 | Lee et al. |
| 7,910,365 B1 | 3/2011 | Sagripanit et al. |
| 7,943,762 B2 | 5/2011 | Weller et al. |
| 7,968,102 B2 | 6/2011 | Quentin-Millet |
| 7,993,844 B1 | 8/2011 | Sagripanti et al. |
| 8,017,330 B1 | 9/2011 | Sagripanti et al. |
| 8,017,754 B2 | 9/2011 | Wicker et al. |
| 8,025,887 B2 | 9/2011 | Kinney et al. |
| 8,039,003 B2 | 10/2011 | Whitehead et al. |
| 8,048,427 B2 | 11/2011 | Pang et al. |
| 8,067,565 B2 | 11/2011 | Kinney et al. |
| 8,067,566 B2 | 11/2011 | Kinney et al. |
| 8,075,903 B2 | 12/2011 | Whitehead et al. |
| 8,278,052 B2 | 10/2012 | Lam et al. |

FOREIGN PATENT DOCUMENTS

| | | | |
|---|---|---|---|
| EP | 1605047 A1 | 12/2005 |
| EP | 2278012 A2 | 1/2011 |
| EP | 2290108 A2 | 3/2011 |
| EP | 2290109 A2 | 3/2011 |
| EP | 2292802 A2 | 3/2011 |
| EP | 2351844 A1 | 8/2011 |
| WO | 9306214 A1 | 4/1993 |
| WO | 9322440 A1 | 11/1993 |
| WO | 9637221 A1 | 11/1996 |
| WO | 9906068 A2 | 2/1999 |
| WO | 9918216 A2 | 4/1999 |
| WO | 0064479 A1 | 11/2000 |
| WO | 0160847 A2 | 8/2001 |
| WO | 0214500 A2 | 2/2002 |
| WO | 02072803 A2 | 9/2002 |
| WO | 02081511 A1 | 10/2002 |
| WO | 02081741 A2 | 10/2002 |
| WO | 02095075 A1 | 11/2002 |
| WO | 2004022784 A2 | 3/2004 |
| WO | 2004097017 A2 | 11/2004 |
| WO | 2005030800 A2 | 4/2005 |
| WO | 2005092059 A2 | 10/2005 |
| WO | 2006134433 A1 | 12/2006 |
| WO | 2006134443 A1 | 12/2006 |
| WO | 2007015783 A2 | 2/2007 |
| WO | 2007031034 A1 | 3/2007 |
| WO | 2007093472 A1 | 8/2007 |
| WO | 2007141259 A1 | 12/2007 |
| WO | 2008007021 A1 | 1/2008 |
| WO | 2008047023 A2 | 4/2008 |
| WO | 2008065315 A1 | 6/2008 |
| WO | 2008147382 A1 | 12/2008 |
| WO | 2008152528 A2 | 12/2008 |
| WO | 2008157136 A1 | 12/2008 |
| WO | 2009134717 A1 | 11/2009 |

OTHER PUBLICATIONS

Das et al. (2008) J. Clinical Microbiol. vol. 46 No. 10 pp. 3276-3284.*

APO Office Action, Australian Patent Application No. 2010286368, Jun. 10, 2014.

EPO Office Action, European Patent Application No. 10748219.2, Jan. 23, 2013.

PCT International Preliminary Examination Report, International Application No. PCT/US10/047399, Mar. 15, 2012.

PCT Written Opinion, International Application No. PCT/US10/047399, Nov. 22, 2010.

PCT Search Report, International Application No. PCT/US10/047399, Nov. 22, 2010.

Callahan et al., "Development and Evaluation of Serotype- and Group-Specific Fluorogenic Reverse Transcriptase PCR (TaqMan) Assays for Dengue Virus," J. Clin. Microbiol., 2001, 29(11):4119-4124, Am Soc. Microbiology, USA.

Chien et al., "Development of Real-Time Reverse Transcriptase PCR Assays to Detect and Serotype Dengue Viruses," J. Clin. Microbiol., 2001, 44(4):1295-1304, Am. Soc. Microbiology, USA.

Guzman et al., "Dengue diagnosis, advances and challenges," Intl. Jnl. of Infect. Dis., 2004, pp. 69-80, Elsevier USA.

Ito et al., "Development and Evaluation of Fluorogenic TaqMan Reverse Transcriptase PCR Assays for Detection of Dengue Virus Types 1 to 4," J. Clin. Microbiol., 2004, 42(12):5935-5937, Am. Soc. Microbiology, USA.

Kong et al., "Rapid detection, serotyping and quantitation of dengue viruses by TaqMan real-time one-step RT-PCT," J. Virol. Meth., 2006, pp. 123-130, Elsevier B.V., USA.

Lanciotti et al., "Rapid Detection and Typing of Dengue Viruses from Clinical Samples by Using Reverse Transcriptase-Polymerase Chain Reaction," J. Clin. Microbiol., 1992,545-551, Am. Soc. Microbiology, USA.

Usawattanakul et al., "Detection of Dengue Viral RNA in Patients' Sera by Nucleic Acid Sequence-Based Amplification (NASBA) and Polymerase Chain Reaction (PCR)," Dengue Bulletin, 2002, vol. 26, pp. 131-139, World Heath Organization, India.

Shu et al., "Development of Group- and Serotype-Specific One-Step SYBR Green I-Based Real-Time Reverse Transcription-PCR Assay for Dengue Virus," J. Clin. Microbiol., 2003, 41(6):2408-2416, Am. Soc. Microbiology, USA.

* cited by examiner

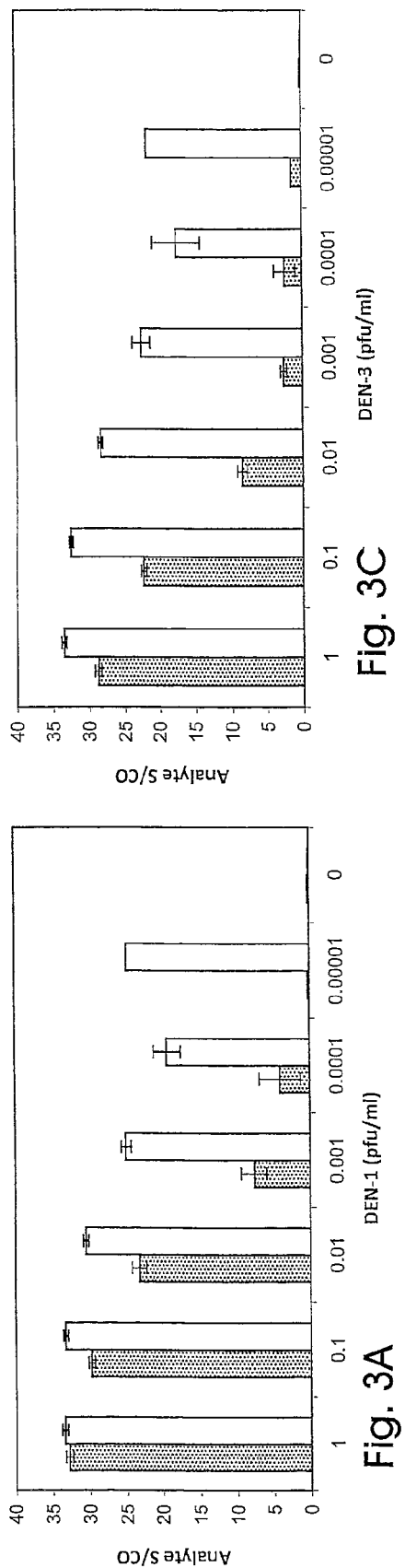
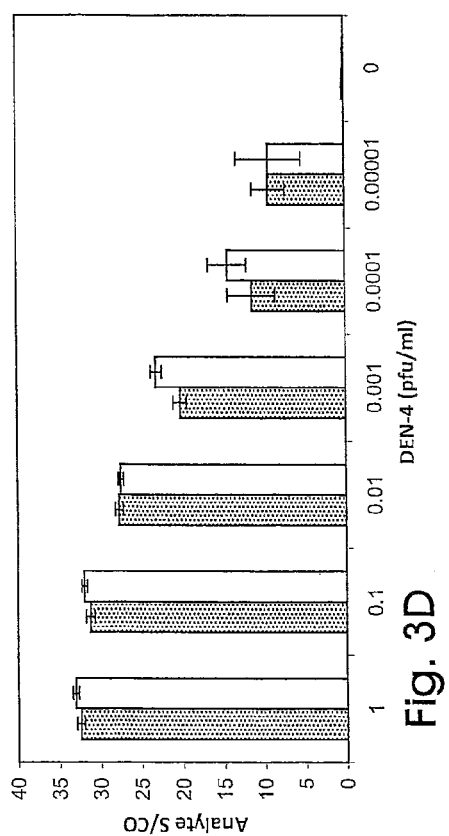
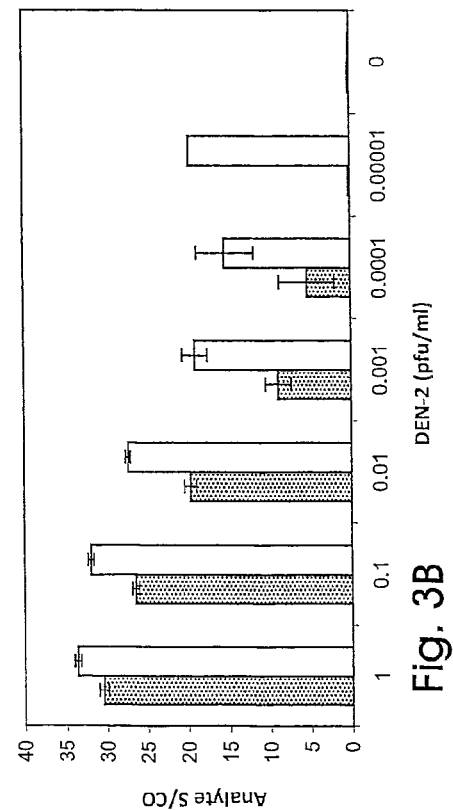
Fig. 3A  Fig. 3B  Fig. 3C  Fig. 3D

SEQUENCE LISTING

```
<160> NUMBER OF SEQ ID NOS: 55

<210> SEQ ID NO 1
<211> LENGTH: 28
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 1
cggtttctcn cgcgtttcag catattga                                            28

<210> SEQ ID NO 2
<211> LENGTH: 28
<212> TYPE: DNA
<213> ORGANISM: Dengue virus
<220> FEATURE:
<221> NAME/KEY: Intron
<222> LOCATION: (10)..(10)
<220> FEATURE:
<221> NAME/KEY: misc_feature
<222> LOCATION: (10)..(10)
<223> OTHER INFORMATION: inosine

<400> SEQUENCE: 2
cggtttctcn cgcgtttcag catattga                                            28

<210> SEQ ID NO 3
<211> LENGTH: 73
<212> TYPE: DNA
<213> ORGANISM: Artificial
<220> FEATURE:
<223> OTHER INFORMATION: Tagged promoter primer
<220> FEATURE:
<221> NAME/KEY: misc_feature
<222> LOCATION: (1)..(27)
<223> OTHER INFORMATION: phage T7 promoter
<220> FEATURE:
<221> NAME/KEY: misc_feature
<222> LOCATION: (28)..(45)
<223> OTHER INFORMATION: tag sequence
<220> FEATURE:
<221> NAME/KEY: misc_feature
<222> LOCATION: (46)..(73)
<223> OTHER INFORMATION: Dengue virus
<220> FEATURE:
<221> NAME/KEY: misc_feature
<222> LOCATION: (55)..(55)
<223> OTHER INFORMATION: inosine

<400> SEQUENCE: 3
aatttaatac gactcactat agggagatat gaatgcgacc cggaacggtt tctcncgcgt    60
```
ttcagcatat tga                                                              73

<210> SEQ ID NO 4
<211> LENGTH: 27
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 4
cggtttctcn cgcgtttcag catattg                                               27

<210> SEQ ID NO 5
<211> LENGTH: 26
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 5
cggtttctcn cgcgtttcag catatt                                                26

<210> SEQ ID NO 6
<211> LENGTH: 25
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 6
cggtttctcn cgcgtttcag catat                                                 25

<210> SEQ ID NO 7
<211> LENGTH: 24
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 7
cggtttctcn cgcgtttcag cata                                                  24

<210> SEQ ID NO 8
<211> LENGTH: 22
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 8
cggtttctcn cgcgtttcag ca                                                    22

<210> SEQ ID NO 9
<211> LENGTH: 21
<212> TYPE: DNA
<213> ORGANISM: Dengue virus
<220> FEATURE:

```
<221> NAME/KEY: misc_feature
<222> LOCATION: (10)..(10)
<223> OTHER INFORMATION: inosine

<400> SEQUENCE: 9
cggtttctcn cgcgtttcag c                                              21

<210> SEQ ID NO 10
<211> LENGTH: 23
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 10
cggtttctcn cgcgtttcag cat                                            23

<210> SEQ ID NO 11
<211> LENGTH: 23
<212> TYPE: DNA
<213> ORGANISM: Dengue virus
<220> FEATURE:
<221> NAME/KEY: misc_feature
<222> LOCATION: (10)..(10)
<223> OTHER INFORMATION: inosine

<400> SEQUENCE: 11
cggtttctcn cgcgtttcag cat                                            23

<210> SEQ ID NO 12
<211> LENGTH: 68
<212> TYPE: DNA
<213> ORGANISM: Artificial
<220> FEATURE:
<223> OTHER INFORMATION: Tagged promoter primer
<220> FEATURE:
<221> NAME/KEY: misc_feature
<222> LOCATION: (1)..(27)
<223> OTHER INFORMATION: phage T7 promoter
<220> FEATURE:
<221> NAME/KEY: misc_feature
<222> LOCATION: (28)..(45)
<223> OTHER INFORMATION: tag sequence
<220> FEATURE:
<221> NAME/KEY: misc_feature
<222> LOCATION: (46)..(68)
<223> OTHER INFORMATION: Dengue virus
<220> FEATURE:
<221> NAME/KEY: misc_feature
<222> LOCATION: (55)..(55)
<223> OTHER INFORMATION: inosine

<400> SEQUENCE: 12
aatttaatac gactcactat agggagatat gaatgcgacc cggaacggtt tctcncgcgt    60
ttcagcat                                                             68

<210> SEQ ID NO 13
<211> LENGTH: 22
<212> TYPE: DNA
<213> ORGANISM: Dengue virus

<400> SEQUENCE: 13
gcttaacrya gttctracag tt                                             22

<210> SEQ ID NO 14
```

```
<211> LENGTH: 22
<212> TYPE: DNA
<213> ORGANISM: Dengue virus

<400> SEQUENCE: 14
gcttaacgta gttctgacag tt                                              22

<210> SEQ ID NO 15
<211> LENGTH: 22
<212> TYPE: DNA
<213> ORGANISM: Dengue virus

<400> SEQUENCE: 15
gcttaacaca gttctaacag tt                                              22

<210> SEQ ID NO 16
<211> LENGTH: 16
<212> TYPE: DNA
<213> ORGANISM: Dengue virus

<400> SEQUENCE: 16
ggaccgacaa gracag                                                     16

<210> SEQ ID NO 17
<211> LENGTH: 16
<212> TYPE: DNA
<213> ORGANISM: Dengue virus

<400> SEQUENCE: 17
ggaccgacaa gaacag                                                     16

<210> SEQ ID NO 18
<211> LENGTH: 16
<212> TYPE: DNA
<213> ORGANISM: Dengue virus

<400> SEQUENCE: 18
ggaccgacaa ggacag                                                     16

<210> SEQ ID NO 19
<211> LENGTH: 17
<212> TYPE: DNA
<213> ORGANISM: Dengue virus
<220> FEATURE:
<221> NAME/KEY: misc_feature
<222> LOCATION: (13)..(13)
<223> OTHER INFORMATION: Pyrimidine or inosine

<400> SEQUENCE: 19
tagagagcag atntctg                                                    17

<210> SEQ ID NO 20
<211> LENGTH: 17
<212> TYPE: DNA
<213> ORGANISM: Dengue virus

<400> SEQUENCE: 20
tagagagcag atctctg                                                    17

<210> SEQ ID NO 21
<211> LENGTH: 17
<212> TYPE: DNA
<213> ORGANISM: Dengue virus
<220> FEATURE:
<221> NAME/KEY: misc_feature
```

```
<222> LOCATION: (13)..(13)
<223> OTHER INFORMATION: Inosine

<400> SEQUENCE: 21
tagagagcag atntctg                                                    17

<210> SEQ ID NO 22
<211> LENGTH: 17
<212> TYPE: DNA
<213> ORGANISM: Dengue virus
<220> FEATURE:
<221> NAME/KEY: misc_feature
<222> LOCATION: (1)..(17)
<223> OTHER INFORMATION: Backbone includes 2'-methoxy residues

<400> SEQUENCE: 22
uagagagcag aucucug                                                    17

<210> SEQ ID NO 23
<211> LENGTH: 17
<212> TYPE: DNA
<213> ORGANISM: Dengue virus
<220> FEATURE:
<221> NAME/KEY: misc_feature
<222> LOCATION: (1)..(17)
<223> OTHER INFORMATION: Backbone includes 2'-methoxy residues

<400> SEQUENCE: 23
uagagagcag auuucug                                                    17

<210> SEQ ID NO 24
<211> LENGTH: 24
<212> TYPE: DNA
<213> ORGANISM: Dengue virus
<220> FEATURE:
<221> NAME/KEY: misc_feature
<222> LOCATION: (1)..(24)
<223> OTHER INFORMATION: Backbone includes 2'-methoxy residues

<400> SEQUENCE: 24
ccacaagcuu agaagauaga gagg                                            24

<210> SEQ ID NO 25
<211> LENGTH: 18
<212> TYPE: DNA
<213> ORGANISM: Dengue virus
<220> FEATURE:
<221> NAME/KEY: misc_feature
<222> LOCATION: (1)..(18)
<223> OTHER INFORMATION: Backbone includes 2'-methoxy residues

<400> SEQUENCE: 25
ucaauaugcu gaaacgcg                                                   18

<210> SEQ ID NO 26
<211> LENGTH: 45
<212> TYPE: DNA
<213> ORGANISM: Artificial
<220> FEATURE:
<223> OTHER INFORMATION: Phage T7 promoter joined upstream of artificial
      tag sequence
<220> FEATURE:
<221> NAME/KEY: misc_feature
<222> LOCATION: (1)..(27)
<223> OTHER INFORMATION: Phage T7 promoter
<220> FEATURE:
<221> NAME/KEY: misc_feature
<222> LOCATION: (28)..(45)
<223> OTHER INFORMATION: Artificial tag sequence
```

-continued

<210> SEQ ID NO 26
<400> SEQUENCE: 26
aatttaatac gactcactat agggagatat gaatgcgacc cggaa          45

<210> SEQ ID NO 27
<211> LENGTH: 18
<212> TYPE: DNA
<213> ORGANISM: Artificial
<220> FEATURE:
<223> OTHER INFORMATION: Artificial tag sequence

<400> SEQUENCE: 27
tatgaatgcg acccggaa          18

<210> SEQ ID NO 28
<211> LENGTH: 27
<212> TYPE: DNA
<213> ORGANISM: Artificial
<220> FEATURE:
<223> OTHER INFORMATION: Phage T7 promoter sequence

<400> SEQUENCE: 28
aatttaatac gactcactat agggaga          27

<210> SEQ ID NO 29
<211> LENGTH: 20
<212> TYPE: RNA
<213> ORGANISM: Dengue virus
<220> FEATURE:
<221> NAME/KEY: misc_feature
<222> LOCATION: (1)..(20)
<223> OTHER INFORMATION: Backbone includes 2'-methoxy residues

<400> SEQUENCE: 29
caugcguaca gcuuccaugg          20

<210> SEQ ID NO 30
<211> LENGTH: 20
<212> TYPE: RNA
<213> ORGANISM: Dengue virus
<220> FEATURE:
<221> NAME/KEY: misc_feature
<222> LOCATION: (1)..(20)
<223> OTHER INFORMATION: Backbone includes 2'-methoxy residues

<400> SEQUENCE: 30
ccuuccacga agucucuguu          20

<210> SEQ ID NO 31
<211> LENGTH: 19
<212> TYPE: RNA
<213> ORGANISM: Dengue virus
<220> FEATURE:
<221> NAME/KEY: misc_feature
<222> LOCATION: (1)..(19)
<223> OTHER INFORMATION: Backbone includes 2'-methoxy residues

<400> SEQUENCE: 31
ugagaaucuc uucgccaac          19

<210> SEQ ID NO 32
<211> LENGTH: 22
<212> TYPE: RNA
<213> ORGANISM: Dengue virus
<220> FEATURE:
<221> NAME/KEY: misc_feature
<222> LOCATION: (1)..(22)

<223> OTHER INFORMATION: Backbone includes 2'-methoxy residues

<400> SEQUENCE: 32
ugagaaucuc uuugucagcu gu　　　　　　　　　　　　　　　　　　　　　22

<210> SEQ ID NO 33
<211> LENGTH: 33
<212> TYPE: DNA
<213> ORGANISM: Artificial
<220> FEATURE:
<223> OTHER INFORMATION: Sequence for hybridizing to oligo(dT) beads

<400> SEQUENCE: 33
tttaaaaaaa aaaaaaaaaa aaaaaaaaaa aaa　　　　　　　　　　　　　　　33

<210> SEQ ID NO 34
<211> LENGTH: 24
<212> TYPE: DNA
<213> ORGANISM: Dengue virus

<400> SEQUENCE: 34
cctctctatc ttctaagctt gtgg　　　　　　　　　　　　　　　　　　　　24

<210> SEQ ID NO 35
<211> LENGTH: 69
<212> TYPE: DNA
<213> ORGANISM: Artificial
<220> FEATURE:
<223> OTHER INFORMATION: Tagged promoter-primer

<400> SEQUENCE: 35
aatttaatac gactcactat agggagatat gaatgcgacc cggaacctct ctatcttcta　　　60 agcttgtgg　　　　　　　　　　　　　　　　　　　　　　　　　　　　　69

<210> SEQ ID NO 36
<211> LENGTH: 1616
<212> TYPE: RNA
<213> ORGANISM: Dengue virus

<400> SEQUENCE: 36
gggcgaauug gguacccagu uguuagucua cguggaccga caagaacagu uucgaaucgg　　　60 aagcuugcuu aacguaguuc ugacaguuuu uauuuagag agcagaucuc ugaugaacaa　　120 ccaacggaaa aagacggguc gaccgucuuu caauaugcug aaacgcgcga gaaaccgcgu　　180 gucaacuguu ucacaguugg cgaagagauu cucaaaagga uugcuuucag gccaaggacc　　240 caugaaauug gugauggcuu uuauagcauu ccuaagauuu cuagccauac ccccaacagc　　300 aggaauuuug gcuagauggg gcucacucaa gaagaaugga gcgauuaaag ugcuacgggg　　360 uuucaagaaa gaaaucucaa acaugcugag cauaaugaau agaagaaaaa gauccgugac　　420 caugcuccuu augcugcugc ccacagcccu ggcguuccau cugaccacac gaggggagag　　480 gccgcacaug auaguuagca agcaggaaag aggagaguca cuuuuguuua agaccucugc　　540 aggugucaac augugcaccc uuauugcgau ggauuuggga gaguuaugug aggacacaau　　600 gaccuacaaa ugcccucgga ucacuaaggc ggaaccagau gacguugacu guuggugcaa　　660 ugccacggac acauggguga ccuauggaac uguguucaa acuggcgaac accgacgaga　　720 caagcguucc gucgcacugg ccccacaugu ggggcuuggu cuagaaacaa gagccgaaac　　780 guggauguuc cucgaaggcg cuuggaaaca aauacaaaaa guggagacuu gggcucugag　　840 acacccagga uucacgguaa uagcccucuu ucuagcacau gccauaggaa cauccaucac　　900

| | | | | |
|---|---|---|---|---|
| ccagaaaggg | auuauuuuca | uuuuguugau | gcugguaaca | ccauccaugg | ccaugcgaug | 960 |
| cgugggaaua | ggcaacagag | acuucgugga | aggacuguca | ggaggaacgu | ggugggaugu | 1020 |
| gguacuggag | cauggaaguu | gcgucaccac | cauggcaaaa | gauaaaccaa | cauuggacau | 1080 |
| ugaacucuug | aagacggagg | ucacaaaccc | ugccguccug | cguaaacugu | gcauugaagc | 1140 |
| uaaaauauca | aacaccacca | ccgauucaag | auguccaaca | caaggggaag | ccacacuggu | 1200 |
| ggaagaacaa | gacgcgaacu | ucgugugucg | acgaacguuu | ggacagag | gcuggggcaa | 1260 |
| uggcuguggg | cuuuucggaa | aagguagccu | aauaacgugu | gcuaaguuca | agugugugac | 1320 |
| aaaacuggaa | ggaaagauug | uucaauauga | gaacuugaaa | uauucaguga | uagucaccgu | 1380 |
| ccacacuggu | gaccagcacc | aggugggaaa | ugagaccaca | gaacauggaa | caauugcaac | 1440 |
| cauaacaccu | caagcccuua | cgucggaaau | acagcugacc | gacacgagg | cucuuacauu | 1500 |
| ggauugcuca | cccagaacag | ggcuagacuu | uaaugagaug | uguuguuga | caaugaaaga | 1560 |
| aaaaucaugg | cauguccaca | aacaaugguu | ucuagacauc | gauaagcuug | auaucg | 1616 |

<210> SEQ ID NO 37
<211> LENGTH: 1557
<212> TYPE: RNA
<213> ORGANISM: Dengue virus

<400> SEQUENCE: 37

| | | | | | |
|---|---|---|---|---|---|
| gggcgaauug | gguacccagu | uguuagucua | cguggaccga | caaagacaga | uucuuugagg | 60 |
| gagcuaagcu | caacguaguu | cuaacaguuu | uuuaauuaga | gagcagaucu | cugaugaaua | 120 |
| accaacgaaa | aaaggcgaga | aauacgccuu | ucaauaugcu | gaaacgcgag | agaaaccgcg | 180 |
| ugucgacugu | acaacagcug | acaaagagau | ucucacuugg | aaugcugcag | ggacgaggac | 240 |
| cauuaaaacu | guucauggcc | cuggugggcgu | uccuucguuu | ccuaacaauc | ccaccaacag | 300 |
| cagggauacu | gaagagaugg | ggaacaauua | aaaaaucaaa | agccauuaau | guuuugagag | 360 |
| gguucaggaa | agagauugga | aggaugcuga | acaucugaa | caggagacgc | agaacugcag | 420 |
| gcaugaucau | uaugcugauu | ccaacaguga | uggcguucca | uuuaaccaca | cgcaacggag | 480 |
| aaccacacau | gaucgucagu | agacaagaga | aagggaaaag | ucuucuguuu | aaaacagggg | 540 |
| augguguaa | caugugcacc | cucauggcca | uggaccuugg | ugaauugugu | gaagauacaa | 600 |
| ucacguacaa | guguccucuu | cucaggcaga | augaaccaga | agacauagau | guuggugca | 660 |
| acucuacguc | cacaugggua | acuuauggga | cguguaccac | cacaggagaa | cacagaagag | 720 |
| aaaaagauc | aguggcacuc | guccacaug | ugggaauggg | acuggagaca | cgaacugaaa | 780 |
| cauggaugc | aucagaaggg | gccuggaaac | augcccagag | aauugaaacu | uggaucuuga | 840 |
| gacauccagg | cuuugccaua | auggcagcaa | uccuggcaua | caccauagga | acgacacauu | 900 |
| uccaaagagc | ccugauuuuc | aucuuacuga | cagcugucgc | uccuucaaug | acaaugcguu | 960 |
| gcauaggaau | ucaaauaga | acuuuguag | aaggggluuc | aggaggaagc | ugguugaca | 1020 |
| uagucuuaga | cauggaagc | ugugugacga | cgauggcaaa | aaacaaacca | acauuggauu | 1080 |
| uugaacugau | aaaaacagaa | gccaaacaac | cugucacucu | aaggaaguac | uguauagagg | 1140 |
| caaagcugac | caacacaaca | acagaaucuc | gcugcccaac | acaaggagaa | cccagccuaa | 1200 |
| augaagagca | ggacaaaagg | uucgucugca | acacuccau | ggugacaga | ggaugggaa | 1260 |
| auggaugugg | auuauuugga | aaggaggca | uugugaccug | ugcuauguuc | acaugcaaaa | 1320 |
| agaacaugaa | aggaaaaguc | gugcaaccag | aaaacuugga | auacaccauu | gugauaacac | 1380 |

| | |
|---|---|
| cucacucagg ggaagagcau gcagucggaa augacacagg aaaacauggc aaggaaauca | 1440 |
| aaauaacacc acagaguucc aucacagaag cagaguugac aggcuauggc acugucacga | 1500 |
| uggagugcuc uccgagaacg ggccucgacu ucaaugagau ggccaagcuu gauaucg | 1557 |

<210> SEQ ID NO 38
<211> LENGTH: 1550
<212> TYPE: RNA
<213> ORGANISM: Dengue virus

<400> SEQUENCE: 38

| | |
|---|---|
| gggcgaauug gguaccgggc ccccccucga ggucgacagu uguuagucua cguggaccga | 60 |
| caagaacagu uucgacucgg aagcuugcuu aacguagugc ugacaguuuu uuauuagaga | 120 |
| gcagaucucu gaugaacaac caacggaaaa agacgggaaa accgucuauc aauaugcuga | 180 |
| aacgcgugag aaaccgugug ucaacuggau cacaguuggc gaagagauuc ucaagaggau | 240 |
| ugcugaacgg ccaaggacca augaaauugg uuauggcguu auagcuuuc ucagauuuc | 300 |
| uagccauucc accgacagca ggagucuugg cuagauggg uaccuuuaag aagucggggg | 360 |
| cuauuaaggu cuuaaaaggc uucaagaagg agaucucaaa caugcugagc auuaucaaca | 420 |
| aacggaaaaa gacaucgcuc ugcucauga ugauguuacc agcaacacuu gcuuccacu | 480 |
| uaacuucacg agauggagag ccgcgcauga uguggggaa gaaugaaaga ggaaaauccc | 540 |
| uacuuuuaa gacagcccucu ggaaucaaca ugugcacacu cauagccaug gauuuggag | 600 |
| agaugugua ugacacgguc acuuacaaau gccccacau uaccgaagug gagccugaag | 660 |
| acauugacug cuggugcaac cuuacaucga caugggugc uuauggaaca ugcaaucaag | 720 |
| cuggagagca uagacgcgau aagagaucag uggcguuagc uccccaugu cggcaugggac | 780 |
| uggacacacg cacucaaacc uggaugucg cugaaggagc uuggagacaa gucgagaagg | 840 |
| uagagacaug ggcccuuagg cacccagggu uuaccauacu agcccuauuu cuugcccauu | 900 |
| acauaggcac uuccuugacc cagaaagugg uuauuuuuau acuauuaaug cugguuaccc | 960 |
| cauccaugac aaugagaugu guggaguag gaaacagaga uuuugugaa ggcccaucgg | 1020 |
| gagcuacgug gguugacgug gugcucgagc acgugggug ugugacuacc auggcuaaga | 1080 |
| acaagcccac gcuggacaua gagcuucaga agaccgaggc cacccaaacug gcgacccuaa | 1140 |
| ggaagcuaug cauugaggga aaaauuacca acauaacaac cgacucaaga gucccaccc | 1200 |
| aaggggaagc gauuuuaccu gaggagcagg accagaacua cgugugcaag cauacauacg | 1260 |
| uggacagagg cuggggaaac gguugugguu uguuggcaa gggaagcuug gugacaugcg | 1320 |
| cgaaauuuca auguuagaa ucauagagg gaaaaguggu gcaacaugag aaccucaaau | 1380 |
| acaccgucau caucacagug cacacaggag accaacacca ggugggaaau gaaacgcagg | 1440 |
| gaguuacggc ugagauaaca ucccaggcau caaccgcuga agccauuuua ccugaauaug | 1500 |
| gaacccucgg gcuagaaugc ucaccacgga caucgauaag cuugauaucg | 1550 |

<210> SEQ ID NO 39
<211> LENGTH: 1716
<212> TYPE: RNA
<213> ORGANISM: Dengue virus

<400> SEQUENCE: 39

| | |
|---|---|
| gggcgaauug gguacccagu uguuagucug uguggaccga caaggacagu uccaaaucgg | 60 |
| aagcuugcuu aacacaguuc uaacaguuug uuuagauaga gagcagaucu cuggaaaaau | 120 |
| gaaccaacga aaaaagguggu uuagaccacc uuucaauaug cugaaacgcg agagaaaccg | 180 |

-continued

```
cguaucaacc ccucaagggu uggugaagag auucucaacc ggacuuuuuu ccgggaaagg      240
acccuuacgg auggugcuag cauucaucac guuuuugcga guccuuucca ucccaccaac      300
agcagggauu cugaaaagau ggggacaguu gaagaaaaac aaggccauca aaauacugac      360
uggauucagg aaggagauag gccgcaugcu gaacaucuug aauggaagaa aaaggucaac      420
aaugacauug cugugcuuga uucccaccgu aauggcguuu cacugucaa caagagaugg       480 cgaaccccuu augauagugg caaaacacga aggggggaga ccucucuugu uaagacaac       540 agagggaauc aacaaaugca cucuuauugc cauggaccug ggugaaaugu gugaggacac      600
cgucacguau gaaugcccuc uacuggucaa uaccgaaccu gaggacauug auugcuggug      660
caaucucacg ucugccuggg ucauguaugg acaugcacu cagagugggg aacggagacg       720
ggagaagcgc ucaguagccc uaacaccaca uucaggaaug gauuggaga caagggcuga       780 gacauggaug ucaucggaag gggcuuggaa acaugcucag aggguagaga guuggauacu      840
cagaaaccca ggauucgcuc ucuuggcagg auuuauggcc uauaugauug gcaaacagg       900 aauccagcga acagucuucu uuguucuaau gaugcugguc gccccauccu acggaaugcg     960
augcguggga gugggggaaca gagacuuugu ggaaggaguc ucagguggag caugggucga    1020
uuuggugcua gaacauggag gauguguucac aaccauggcc cagggaaaac caaccuugga    1080
uuuugaacug aucaagacaa cagccaagga aguggcucug uuaagaaccu auugcauuga    1140
agccucgaua ucaaacauaa ccacggcaac aagaugucca acgcaaggag aaccuuaucu    1200
caaagaggaa caagaucaac aguacauuug ccggagagau guguagaca gagggugggg     1260 caauggcugu ggcuuguuug ggaaggagg aguugugaca ugugcaagu uucaugcuc       1320 ggggaagaua acaggcaauu ugguccaaau ugagaaccuu gaauacacag uaguuguaac    1380
aguccacaau ggagacaccc augcaguagg aaaugacaua cccaaccaug gagugacagc    1440
cacgauaacc cccaggucac caucggauaga aguuaaauua ccggauuuau gagaauuaac    1500
acucgauugu gaacccaggu ccggaauuga uuuuaaugag augauucuga ugaaaaugaa    1560
aaagaaaacg uggcuugugc acaagcaaug guuuuuggau cuaccucuac cauggcagc     1620 aggagcagac acaucagaag uucauuggaa uuacaaagag agaaugguga cauucaaggu    1680
uccucaugcc aagagacauc gauaagcuug auaucg                              1716
```

<210> SEQ ID NO 40
<211> LENGTH: 1623
<212> TYPE: RNA
<213> ORGANISM: Dengue virus

<400> SEQUENCE: 40

```
gggcgaauug gguacccagu guuagucua cguggaccga caagaacagu uucgaaucgg       60
aagcuugcuu aacguaguuc ugacaguuuu uuauuccaca agcuuagaag auagagagga     120
ugaacaacca acggaaaag acgggucgac cgucuuucaa uaugcugaaa cgcgcgagaa     180
accgcguguc aacuguuuca caguuggcga agagauucuc aaaaggauug cuucaggcc     240 aaggacccau gaaauuggug auggcuuuua uagcauuccu aagauuucua gccauacccc    300
caacagcagg aauuuuggcu agauggggcu cacucaagaa gaauggagcg auuaaagugc    360
uacgggguuu caagaaagaa aucucaaaca ugcugagcau aaugaauaga agaaaaagau    420
ccgugaccau gcuccuuaug cugcugccca gcccuggc guuccaucug accacacgag       480 ggagagcc gcacaugaua guuagcaagc aggaaagagg agagucaccu uuguuuaaga    540
```

| | |
|---|---|
| ccucugcagg ugucaacaug ugcacccuua uugcgaugga uuugggagag uuaugugagg | 600 |
| acacaaugac cuacaaaugc ccucggauca cuaaggcgga accagaugac guugacuguu | 660 |
| ggugcaaugc cacggacaca uggguugaccu auggaacgug uucucaaacu ggcgaacacc | 720 |
| gacgagacaa gcguuccguc gcacuggccc cacaugyggg gcuugucua gaaacaagag | 780 |
| ccgaaacgug gauguccucu gaaggcgcuu ggaaacaaau acaaaaagug gagacuuggg | 840 |
| cucugagaca cccaggauuc acgguaauag cccucuuucu agcacaugcc auaggaacau | 900 |
| ccaucacccca gaaagggauu auuucauuu uguugaugcu gguaacacca uccauggcca | 960 |
| ugcgaugcgu gggaauaggc aacagagacu cguggaagg acugucagga ggaacguggg | 1020 |
| uggaugguggu acuggagcau ggaaguugcg ucaccaccau ggcaaaagau aaaccaacau | 1080 |
| uggacauuga acucuugaag acggagguca caaacccug cguccugcgu aaacugugca | 1140 |
| uugaagcuaa aauaucaaac accaccaccg auucaagaug ccaacacaa ggggaagcca | 1200 |
| cacuggugga agaacaagac gcgaacuucg uguqucgacg aacguuugug gacagaggcu | 1260 |
| ggggcaaugg cuguggcuu uucggaaaag guagccuaau aacgugugcu aaguucaagu | 1320 |
| gugugacaaa acuggaagga aagauuguuc aauaugagaa cuugaaauau ucagugauag | 1380 |
| ucaccgucca cacuggugac cagcaccagg ugggaaauga gaccacagaa cauggaacaa | 1440 |
| uugcaaccau aacaccucaa gcuccuacgu cggaaauaca gcugaccgac uacggagcuc | 1500 |
| uuacauugga uugcucaccc agaacagggc uagacuuuaa ugagauggug uguuugacaa | 1560 |
| ugaaagaaaa aucauggcau guccacaaac aauggguuucu agacaucgau aagcuugaua | 1620 |
| ucg | 1623 |

<210> SEQ ID NO 41
<211> LENGTH: 1616
<212> TYPE: RNA
<213> ORGANISM: Dengue virus

<400> SEQUENCE: 41

| | |
|---|---|
| gggcgaauug gguacccagu uguuagucua cguggaccga caagaacagu uucgaaucgg | 60 |
| aagcuugcuu aacguaguuc ugacaguuuu uauuuagag agcagaucuc ugaugaacaa | 120 |
| ccaacggaaa aagacgggguc gaccgucuuc cacaagcuua gaagauagag aggaccgcgu | 180 |
| gucaacuguu ucacaguugg cgaagagauu ucaaaaggaa uugcuuucag gccaaggacc | 240 |
| caugaaauug gugauggcuu uuauagcauu ccuaagauuu cuagccauac ccccaacagc | 300 |
| aggaauuuug gcuagauggg gcucacucaa gaagaaugga gcgauuaaag ugcuacgggg | 360 |
| uuucaagaaa gaaaucucaa acaugcugag cauaaugaau agaagaaaaa gauccgugac | 420 |
| caugcucccuu augcugcgc ccacagcccu ggcguuccau cugaccacac gagggggaga | 480 |
| gccgcacaug auaguuagca agcaggaaag aggagaguca cuuuguuuua agaccucugc | 540 |
| aggugucaac augugcaccc uuaugcgau ggauuuggga gaguuaugug aggacacaau | 600 |
| gaccuacaaa ugcccucgga ucacuaaggc ggaaccagau gacguugacu guuggugcaa | 660 |
| ugccacggac acaugggugga ccuauggaac guguucucaa acuggcgaac accgacgaga | 720 |
| caagcguucc gucgcacugg ccccacaugu ggggcuuggu cuagaaacaa gagccgaaac | 780 |
| guggauguccc ucugaaggcg cuuggaaaca aauacaaaaa guggagacuu gggcucugag | 840 |
| acacccagga uucacgguaa uagcccucuu ucuagcacau gccauaggaa cauccaucac | 900 |
| ccagaaaggg auuauuuuca uuuguugau gcugguaaca ccauccaugg ccaugcgaug | 960 |
| cgugggaaua ggcaacagag acuucgugga aggacuguca ggaggaacgu ggguggaugu | 1020 |

-continued

```
gguacuggag cauggaaguu gcgucaccac cauggcaaaa gauaaaccaa cauuggacau    1080
ugaacucuug aagacggagg ucacaaaccc ugccguccug cguaaacugu gcauugaagc    1140
uaaaauauca aacaccacca ccgauucaag auguccaaca caaggggaag ccacacuggu    1200
ggaagaacaa gacgcgaacu ucgugugucg acgaacguuu guggacagag gcuggggcaa    1260
uggcuguggg cuuucggaa aagguagccu aauaacgugu gcuaaguuca agugugugac     1320
aaaacuggaa ggaaagauug uucaauauga gaacuugaaa uauucaguga uagcaccgu     1380 ccacacuggu gaccagcacc aggugggaaa ugagaccaca gaacauggaa caauugcaac    1440
cauaacaccu caagcuccua cgucggaaau acagcugacc gacuacgag cucuuacauu     1500 ggauugcuca cccagaacag ggcuagacuu uaaugagaug guguuguuga caaugaaaga    1560
aaaaucaugg cauguccaca aacaaugguu ucuagacauc gauaagcuug auaucg        1616
```

<210> SEQ ID NO 42
<211> LENGTH: 27
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 42
cggtttctcn cgcgtttcag catattg                                          27

<210> SEQ ID NO 43
<211> LENGTH: 26
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 43
cggtttctcn cgcgtttcag catatt                                           26

<210> SEQ ID NO 44
<211> LENGTH: 25
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 44
cggtttctcn cgcgtttcag catat                                            25

<210> SEQ ID NO 45
<211> LENGTH: 24
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 45
cggtttctcn cgcgtttcag cata                                                    24

<210> SEQ ID NO 46
<211> LENGTH: 22
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 46
cggtttctcn cgcgtttcag ca                                                      22

<210> SEQ ID NO 47
<211> LENGTH: 21
<212> TYPE: DNA
<213> ORGANISM: Dengue virus
<220> FEATURE:
<221> NAME/KEY: misc_feature
<222> LOCATION: (10)..(10)
<223> OTHER INFORMATION: N may be any of A, G, C or T/U; preferably D;
      or I

<400> SEQUENCE: 47
cggtttctcn cgcgtttcag c                                                       21

<210> SEQ ID NO 48
<211> LENGTH: 29
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 48
acggtttctc ncgcgtttca gcatattga                                               29

<210> SEQ ID NO 49
<211> LENGTH: 28
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 49
acggtttctc ncgcgtttca gcatattg                                                28

<210> SEQ ID NO 50
<211> LENGTH: 27
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 50
acggtttctc ncgcgtttca gcatatt                                                 27

<210> SEQ ID NO 51

```
<211> LENGTH: 26
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 51
acggtttctc ncgcgtttca gcatat                                          26

<210> SEQ ID NO 52
<211> LENGTH: 25
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 52
acggtttctc ncgcgtttca gcata                                           25

<210> SEQ ID NO 53
<211> LENGTH: 24
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 53
acggtttctc ncgcgtttca gcat                                            24

<210> SEQ ID NO 54
<211> LENGTH: 23
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 54
acggtttctc ncgcgtttca gca                                             23

<210> SEQ ID NO 55
<211> LENGTH: 22
<212> TYPE: DNA
<213> ORGANISM: Dengue virus
<220> FEATURE:
<221> NAME/KEY: misc_feature
<222> LOCATION: (11)..(11)
<223> OTHER INFORMATION: N may be any of A, G, C or T/U; preferably D;
      or I

<400> SEQUENCE: 55
acggtttctc ncgcgtttca gc                                              22
```

DENGUE VIRUS ASSAY

RELATED APPLICATION

This application claims the benefit of U.S. Provisional Application No. 61/238,637, filed Aug. 31, 2009. The entire disclosure of this prior application is hereby incorporated by reference.

FIELD OF THE INVENTION

The present invention relates to the fields of molecular biology and biotechnology. More specifically, the invention relates to nucleic acid amplification-based assays for detecting Dengue virus.

BACKGROUND OF THE INVENTION

Dengue, which is the most common arthropod-borne infection worldwide, affects at least 50 million people every year. (Teo et al., *Transfusion Medicine* 19:66-77 (2009)) The group of viruses responsible for causing Dengue fever and Dengue hemorrhagic fever is endemic in more than 100 countries, and consists of four antigenically related virus serotypes called DEN-1, DEN-2, DEN-3 and DEN-4 (i.e., Dengue-1, Dengue-2, Dengue-3 and Dengue-4, respectively). Despite extensive cross-reactivity among these viruses in serological tests, there is no cross-protective immunity in humans. Individuals living in an endemic area can have as many as four infections, one with each serotype, during their lifetimes. (Mackenzie et al., *Nature Medicine Supplement* 10:S98-S109 (2004)) Notably, nearly 2.5 billion people are at risk of infection with Dengue virus, and 500,000 hospitalizations are required each year as a result. (Teo et al., supra)

The Dengue viruses are the only known arboviruses that have fully adapted to humans. The principal mosquito vector, *Ae. aegypti*, is a highly domesticated insect that prefers feeding on humans, and laying eggs in artificial containers in and around houses. *Ae. aegypti* is an efficient epidemic vector of Dengue virus because it often feeds on, and thus transmits virus to, more than one individual in a single gonotrophic cycle. Secondary vectors of Dengue virus include *Ae. albopictus* and *Ae. polynesiensis*. Although the virus may be transmitted vertically from an infected female to her offspring, most mosquitoes become infected when they ingest blood from a person experiencing an accute infection. (Mackenzie et al., supra) The increased incidence of epidemic Dengue fever and Dengue hemorrhagic fever in the human population has been attributed to factors including: (1) increased population growth and urbanization, especially in tropical developing countries, (2) lack of effective mosquito control, including increased geographic distribution of *Ae. aegypti*, and (3) increased air travel which provides a means for transporting Dengue and other urban pathogens between population centers of the world. (Gubler, *Clin. Microl. Rev.* 11:480-496 (1998))

While other parts of the world may be more severely impacted, the emergence of Dengue-related disease as a major public health problem has been most dramatic in the American region. In 1970, only DEN-2 was present in the Americas, although DEN-3 may have had a focal distribution in Columbia and Puerto Rico. In 1977, DEN-1 was introduced and caused major epidemics throughout the region over a 16-year period. DEN-4 was introduced in 1981 and caused similar widespread epidemics. Also in 1981, a new strain of DEN-2 from Southeast Asia caused the first major DHF epidemic in the Americas (Cuba). DEN-3 virus recently reappeared in the Americas after an absence of 16 years. Indeed, there is a small, but significant, risk for Dengue outbreaks in the continental United States, which harbors two competent mosquito vectors (i.e., *Ae. aegypti* and *Ae. albopictus*) that are capable of transmitting Dengue viruses. (Gubler et al., *Emerg Infect Dis* 1:55-57 (1995)) Today all four serotypes are broadly distributed across virtually all regions of the world that harbor Dengue virus. (Mackenzie et al., supra)

Although the major route of transmission occurs through the *Ae. aegypti* mosquito vector, Dengue virus has also been transmitted through blood and organ transplantation. (Teo et al., supra) For example, transmission of Dengue infection has been reported from donor to recipient in one case of living donor renal transplant. Transmission during a bone marrow transplant was reported in one instance during a Dengue epidemic in Puerto Rico in 1994. One instance of transmission through blood transfusion involved a patient in Hong Kong who developed fever and other symptoms three days after a blood transfusion. The donor was asymptomatic at the time of donation but developed mild symptoms of Dengue fever one day after blood donation. An archived sample from the donation also tested positive for Dengue virus by RT-PCR. Another instance of transfusion-related illness involved the transmission of Dengue from an asymptomatic blood donor who developed an acute febrile illness the day after donating blood. Retrospective investigation confirmed Dengue infection in the recipients of the three blood products from his donation. Two recipients had Dengue fever with some evidence of capillary leakage, whereas the platelet recipient had asymptomatic seroconversion. All recovered without sequelae. A stored serum sample from the donation tested positive for DEN-2 by RT-PCR. (Teo et al., supra)

While there may be clear reason for wanting to detect all four Dengue serotypes, implementation of a single assay that is highly sensitive for all serotypes has been hampered by limited relatedness of the viral targets at the nucleic acid level. For example, Forattini in *Dengue Bulletin* 27:91-94 (2003), and Domingo et al., in *Dengue Bulletin* 28:87-95 (2004) have both presented phylogenetic trees showing that DEN-4 is highly diverged from the remaining three serotypes.

Previous attempts by others to create nucleic acid-based assays for detecting Dengue virus have met with some success. For example, Usawattanakul et al., in *Dengue Bulletin* 26:125-130 (2002), describe a transcription-based nucleic acid amplification assay able to detect all four Dengue serotypes in the 3' region of the viral genome with a sensitivity equal to 1 PFU/ml (see Abstract). The authors present electrophoretic results indicating a graded decrease in the amount of amplification product synthesized at different input levels of the four Dengue serotypes. No amplification product was detected below 0.1 PFU/ml for any of the Dengue targets. Notably, the target-complementary sequences of the primers and probe employed by Usawattanakul et al., are substantially identical to oligonucleotide sequences disclosed in U.S. Pat. No. 6,333,6150.

Our own efforts to create a sensitive assay using the 3' region of the viral genome as a target for amplification resulted in an assay having an approximately ten-fold improvement in sensitivity for all four serotypes. However, that assay was characterized by dramatically different sensitivities for the different serotypes at very low levels of input target. In our hands, 100% of DEN-2 was detected at a concentration of 0.001 PFU/ml, but DEN-1 was detected in only 20% of the cases. Accordingly, there remains a need for an amplified assay that is both highly sensitive, and similarly sensitive for all four Dengue virus serotypes.

SUMMARY OF THE INVENTION

In one aspect, the invention relates to a method of determining whether a test sample contains Dengue virus. In accordance with the method, first there is a step for obtaining nucleic acids from the test sample. Next, there is a step for performing an in vitro nucleic acid amplification reaction using the obtained nucleic acids as templates for amplification using a set of primers. If the test sample included nucleic acids of any of Dengue virus serotypes 1-4 at a concentration as low as 20 copies/ml, then an amplification product will be produced in the amplification reaction. The 3' terminal base sequence of a first member of the set of primers consists of a target-hybridizing sequence that is any of SEQ ID NO:1 and SEQ ID NO:10, optionally joined to an upstream promoter sequence, and further optionally joined to an upstream tag sequence, wherein neither the upstream promoter sequence nor the upstream tag sequence can hybridize to the nucleic acid of any of Dengue virus serotypes 1-4 and participate in the in vitro nucleic acid amplification reaction in the absence of joining to the target-hybridizing sequence. The upstream tag sequence can be positioned between the target-hybridizing base sequence and the upstream promoter sequence. As well, the 3' terminal base sequence of a second member of the set of primers consists of SEQ ID NO:13. Finally, there is a step for detecting any of the amplification product that may have been produced in the in vitro nucleic acid amplification reaction. Detecting the amplification product determines that the test sample contains at least one of Dengue virus serotypes 1-4. Conversely, the absence of detecting the amplification product, or failing to detect the amplification product determines that the test sample does not contain Dengue virus. In one preferred embodiment, the obtaining step can involve capturing nucleic acids from the test sample onto a solid support, and then isolating the solid support. In another preferred embodiment, the in vitro nucleic acid amplification reaction in the performing step is an isothermal in vitro nucleic acid amplification reaction. In another preferred embodiment, the detecting step can involve detecting by a procedure that is either luminometry or fluorometry. In another preferred embodiment, the detecting step can involve detecting a chemiluminescent signal by luminometry. In another preferred embodiment, the base sequence of the first member of the set of primers in the performing step consists of the target-hybridizing sequence of SEQ ID NO:1 joined to the upstream promoter sequence. When this is the case, the set of primers in the performing step preferably may further include an additional member, the base sequence of this additional member being the target-hybridizing sequence of SEQ ID NO:10 joined to the upstream promoter sequence. Still more preferably, the set of primers in the performing step may further include SEQ ID NO:16. Still more preferably, the detecting step involves contacting the amplification product with a detectably labeled hybridization probe. Yet still more preferably, the base sequence of the detectably labeled hybridization probe is SEQ ID NO:19 or the complement thereof, allowing for substitution of RNA and DNA equivalent bases. In accordance with a different preferred embodiment, the base sequence of the first member of the set of primers in the performing step consists of the target-hybridizing sequence of SEQ ID NO:10 joined to the upstream promoter sequence. When this is the case, the set of primers in the performing step further may include an oligonucleotide of SEQ ID NO:16. In accordance with yet a different preferred embodiment, the detecting step may involve measuring an optical signal, and then comparing the measured optical signal to a cutoff value. Generally speaking, preferred test samples include any of blood, blood products, and serum.

In another aspect, the invention relates to a method for determining whether a test sample contains Dengue virus. In accordance with this method, first there is a step for obtaining nucleic acids from the test sample. Next, there is a step for performing an in vitro nucleic acid amplification reaction using the obtained nucleic acids as templates for amplification using a set of primers. If the test sample included nucleic acids of any of Dengue virus serotypes 1-4 at a concentration as low as 50 copies/ml, there will be produced an amplification product. The 3' terminal base sequence of a first member of the set of primers consists of a target-hybridizing sequence that may be any of SEQ ID NO:1 and SEQ ID NO:10, optionally joined to an upstream promoter sequence, and further optionally joined to a tag sequence. The upstream tag sequence can be positioned between the target-hybridizing base sequence and the upstream promoter sequence. Neither the optional upstream promoter sequence nor the optional tag sequence is capable of hybridizing to the nucleic acids of any of Dengue virus serotypes 1-4 to participate in the in vitro nucleic acid amplification reaction in the absence of joining to the target-hybridizing sequence. The 3' terminal base sequence of a second member of the set of primers consists of SEQ ID NO:19, allowing for RNA and DNA equivalent base substitutions. Finally, there is a step for detecting any of the amplification product that may have been produced in the in vitro nucleic acid amplification reaction. Detecting the amplification product determines that the test sample contains at least one of Dengue virus serotypes 1-4. Conversely, not detecting, or failing to detect the amplification product determines that the test sample does not contain Dengue virus. In one preferred embodiment, the base sequence of the first member of the set of primers consists of the target-hybridizing sequence of SEQ ID NO:1, optionally joined to the upstream promoter sequence, and further optionally joined to the tag sequence between the target-hybridizing sequence and the upstream promoter sequence. In such an instance, the base sequence of the first member of the set of primers may consist of the target-hybridizing sequence of SEQ ID NO:1 joined to the upstream promoter sequence, and further joined to the tag sequence, where the tag sequence is positioned between the target-hybridizing sequence and the upstream promoter sequence. More preferably, the set of primers further includes a tagged promoter primer that hybridizes to the complement of the tag sequence which is contained in extension products of the second member of the set of primers to participate in the in vitro nucleic acid amplification reaction. Alternatively, when the base sequence of the first member of the set of primers consists of the target-hybridizing sequence of SEQ ID NO:1, optionally joined to the upstream promoter sequence, and further optionally joined to the tag sequence between the target-hybridizing sequence and the upstream promoter sequence, it is preferred that the in vitro nucleic acid amplification reaction is an isothermal nucleic acid amplification reaction. In a different preferred embodiment, the in vitro nucleic acid amplification reaction is an isothermal nucleic acid amplification reaction. In still a different preferred embodiment, the obtaining step involves capturing nucleic acids from the test sample onto a solid support, and then washing the solid support to remove material not captured thereon. In still yet a different preferred embodiment, the detecting step may involve contacting the amplification product with a detectably labeled hybridization probe. In a particular instance, the detectably labeled hybridization probe is complementary to the target-hybridizing sequence of SEQ ID NO:1.

In another aspect, the invention relates to a composition for amplifying the nucleic acids of Dengue virus serotypes 1-4 in a nucleic acid amplification reaction. The invented composition includes at least one first-strand priming oligonucleotide. The 3' terminal base sequence of the at least one first-strand priming oligonucleotide consists of a target-hybridizing sequence that may be either of SEQ ID NO:1 and SEQ ID NO:10, optionally joined to an upstream promoter sequence, and further optionally joined to an upstream tag sequence. The upstream tag sequence can be positioned between the target-hybridizing base sequence and the upstream promoter sequence. Neither the optional upstream promoter sequence nor the optional upstream tag sequence can hybridize to any Dengue virus nucleic acid and participate in the nucleic acid amplification reaction in the absence of joining to the target-hybridizing sequence. As well, there is at least one second-strand priming oligonucleotide. The 3' terminal base sequence of one of the at least one second-strand priming oligonucleotides consists of SEQ ID NO:13. Notably, the invented composition detectably amplifies nucleic acids of Dengue virus serotypes 1-4 when present in amounts as low as 10 copies per 100 µl of reaction volume at the start of the nucleic acid amplification reaction. In accordance with one preferred embodiment, the at least one first-strand priming oligonucleotide includes two first-strand priming oligonucleotides. The base sequence of one of the two first-strand priming oligonucleotides is SEQ ID NO:1, optionally joined to the upstream promoter sequence. The base sequence of the other of the two first-strand priming oligonucleotides is SEQ ID NO:10, optionally joined to the upstream promoter sequence. More preferably, each of the two first-strand priming oligonucleotides includes the upstream promoter sequence. Still more preferably, the at least one second-strand priming oligonucleotide further includes an additional second-strand priming oligonucleotide. The base sequence of this additional second-strand priming oligonucleotide consists of SEQ ID NO:16. In accordance with a second preferred embodiment, the at least one second-strand priming oligonucleotide further includes an additional second-strand priming oligonucleotide. The base sequence of the additional second-strand priming oligonucleotide consisting of SEQ ID NO:16.

In another aspect, the invention relates to a kit for use in detecting the nucleic acids of each of Dengue virus serotypes 1-4 in a nucleic acid amplification reaction. The kit includes in a packaged combination of one of more containers two key components. First, there is at least one first-strand priming oligonucleotide. The 3' terminal base sequence of the at least one first-strand priming oligonucleotide consists of a target-hybridizing base sequence that may be either of SEQ ID NO:1 and SEQ ID NO:10, optionally joined to an upstream promoter sequence, and further optionally joined to an upstream tag sequence. The upstream tag sequence can be positioned between the target-hybridizing base sequence and the upstream promoter sequence. Neither the upstream promoter sequence nor the tag sequence hybridizes to any Dengue virus nucleic acid and participates in the nucleic acid amplification reaction in the absence of joining to the target-hybridizing base sequence. Second, there is a second oligonucleotide, the 3' terminal base sequence of which consists of SEQ ID NO:19, allowing for RNA and DNA equivalent base substitutions. In one preferred embodiment, the base sequence of the at least one first-strand priming oligonucleotide consists of SEQ ID NO:1 joined to both the upstream promoter sequence and the upstream tag sequence. In this instance, the second oligonucleotide is a priming oligonucleotide that includes a DNA backbone. More preferably, the kit further includes a tagged promoter oligonucleotide that consists of the tag sequence joined to the upstream promoter sequence. In a different preferred embodiment, the kit further includes a second-strand priming oligonucleotide. The base sequence of the second-strand priming oligonucleotide is SEQ ID NO:13. The second oligonucleotide is a hybridization detection probe in this embodiment. Further, the at least one first-strand priming oligonucleotide and the second-strand priming oligonucleotide, when combined in the nucleic acid amplification reaction detectably amplify nucleic acids of Dengue virus serotypes 1-4 when present in amounts as low as 10 copies per 100 μl of reaction volume at the start of the nucleic acid amplification reaction. More preferably, the kit further includes an additional second-strand priming oligonucleotide. The base sequence of this additional second-strand priming oligonucleotide consists of SEQ ID NO:16. In a different preferred embodiment, the at least one first-strand priming oligonucleotide includes two first-strand priming oligonucleotides. The base sequence of one of the two first-strand priming oligonucleotides is SEQ ID NO:1, optionally joined to the upstream promoter sequence. The base sequence of the other of the two first-strand priming oligonucleotides is SEQ ID NO:10, optionally joined to the upstream promoter sequence. More preferably, each of the two first-strand priming oligonucleotides includes the upstream promoter sequence. Still more preferably, the kit further includes a second-strand priming oligonucleotide, where the base sequence consists of SEQ ID NO:13. As well, there is an additional second-strand priming oligonucleotide, the base sequence of which consists of SEQ ID NO:16. Here the second oligonucleotide with the base sequence of SEQ ID NO:19 is a hybridization detection probe. In accordance with other preferred embodiments, where the base sequence of the at least one first-strand priming oligonucleotide consists of SEQ ID NO:1 joined to both the upstream promoter sequence and the tag sequence, and where the second oligonucleotide is a priming oligonucleotide that includes a DNA backbone, the kit further includes a probe oligonucleotide. For example, the base sequence of the probe oligonucleotide can be SEQ ID NO:25. In still a different preferred embodiment, the kit further includes a second-strand priming oligonucleotide, where the base sequence of the second-strand priming oligonucleotide consists of SEQ ID NO:13, and where the second oligonucleotide is a hybridization detection probe.

In another aspect, the invention relates to a kit for detecting the nucleic acids of each of Dengue virus serotypes 1-4 in a nucleic acid amplification reaction. The kit includes a packaged combination of two key components. First, there is at least one first-strand priming oligonucleotide up to 73 bases in length. The 3' terminal base sequence of the at least one first-strand priming oligonucleotide consists of a target-hybridizing base sequence given by any of SEQ ID NO:1, SEQ ID NO:10, and SEQ ID NOs:42-47 optionally joined to an upstream promoter sequence, and further optionally joined to an upstream tag sequence. The upstream tag sequence can be positioned between the target-hybridizing base sequence of the at least one first-strand priming oligonucleotide and the upstream promoter sequence. Neither the upstream promoter sequence nor the tag sequence is able to hybridize to any Dengue virus nucleic acid and participate in the nucleic acid amplification reaction in the absence of joining to the target-hybridizing base sequence. Second, there is at least one second-strand priming oligonucleotide that hybridizes to an extension product of the at least one first-strand priming oligonucleotide using any of SEQ ID NOs:36-39 as a template. Generally speaking, the first-strand and second-strand priming oligonucleotides in combination are capable of detectably amplifying nucleic acids of Dengue virus serotypes 1-4 when present in amounts as low as 10 copies per 100 µl of reaction volume at the start of the nucleic acid amplification reaction. In a preferred embodiment, the base sequence of the at least one second-strand priming oligonucleotide is of SEQ ID NO:19, allowing for RNA and DNA equivalent base substitutions. In a different preferred embodiment, the base sequence of the at least one second-strand priming oligonucleotide is of SEQ ID NO:13. In yet a different preferred embodiment, the base sequence of the at least one second-strand priming oligonucleotide is of SEQ ID NO:16. In still yet a different preferred embodiment, position 10 of the target-hybridizing base sequence of the at least one first-strand priming oligonucleotide is occupied by inosine.

In another aspect, the invention relates to a kit for detecting the nucleic acids of Dengue virus serotype 3 in a nucleic acid amplification reaction. The kit includes a packaged combination of two key components. First, there is at least one first-strand priming oligonucleotide up to 73 bases in length. The 3' terminal base sequence of the at least one first-strand priming oligonucleotide consists of a target-hybridizing base sequence given by any of SEQ ID NOs:48-55 optionally joined to an upstream promoter sequence, and further optionally joined to an upstream tag sequence. The upstream tag sequence can be positioned between the target-hybridizing base sequence of the at least one first-strand priming oligonucleotide and the upstream promoter sequence. Neither the upstream promoter sequence nor the tag sequence is able to hybridize to any Dengue virus nucleic acid and participate in the nucleic acid amplification reaction in the absence of joining to the target-hybridizing base sequence. Second, there is at least one second-strand priming oligonucleotide that hybridizes to an extension product of the at least one first-strand priming oligonucleotide using any of SEQ ID NOs:36-39 as a template. Generally speaking, the first-strand and second-strand priming oligonucleotides in combination are capable of detectably amplifying nucleic acids of Dengue virus serotypes 1-4 when present in amounts as low as 10 copies per 100 µl of reaction volume at the start of the nucleic acid amplification reaction. In a preferred embodiment, the base sequence of the at least one second-strand priming oligonucleotide is of SEQ ID NO:19, allowing for RNA and DNA equivalent base substitutions. In a different preferred embodiment, the base sequence of the at least one second-strand priming oligonucleotide is of SEQ ID NO:13. In yet a different preferred embodiment, the base sequence of the at least one second-strand priming oligonucleotide is of SEQ ID NO:16. In still yet a different preferred embodiment, position 10 of the target-hybridizing base sequence of the at least one first-strand priming oligonucleotide is occupied by inosine.

BRIEF DESCRIPTION OF THE DRAWINGS

FIG. 1A illustrates the arrangement of oligonucleotides employed in Examples 1-2. FIG. 1B illustrates the arrangement of oligonucleotides employed in Example 3. FIG. 1C illustrates the arrangement of oligonucleotides employed in Example 4.

FIG. 2A presents results for Dengue virus serotype 1. FIG. 2B presents results for Dengue virus serotype 2. FIG. 2C presents results for Dengue virus serotype 3. FIG. 2D presents results for Dengue virus serotype 4.

FIGS. 3A-3D are a series of bar graphs representing Signal-to-Cutoff (S/CO) values as a function of Dengue virus sample concentration measured in PFU/ml (plaque forming units/ml). Results obtained using the invented 5' region assay are shown using open bars. Results obtained using a comparative 3' region assay are shown using stippled bars. FIG. 2A presents results for Dengue virus serotype 1. FIG. 2B presents results for Dengue virus serotype 2. FIG. 2C presents results for Dengue virus serotype 3. FIG. 2D presents results for Dengue virus serotype 4.

DEFINITIONS

Figure 1:
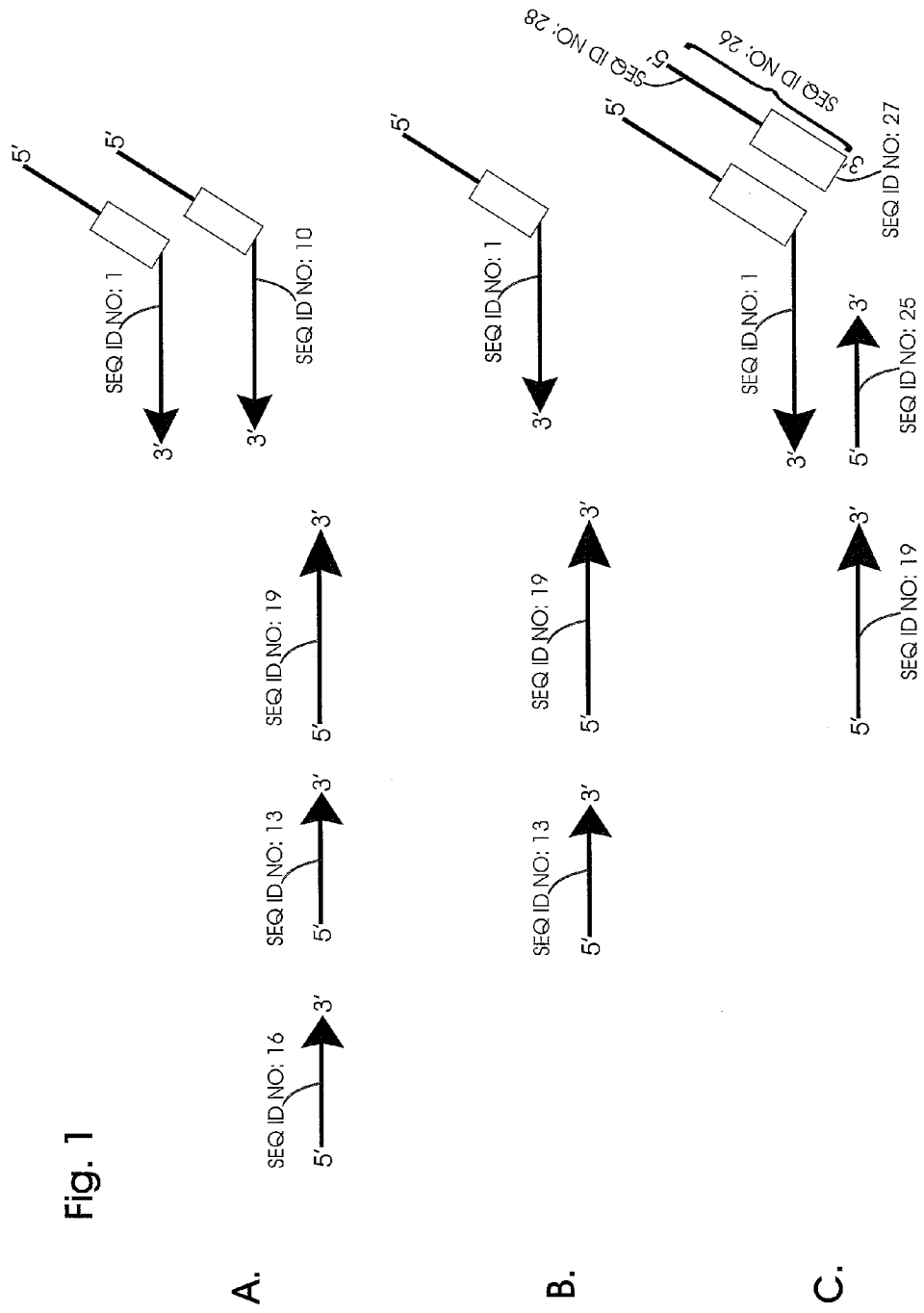
FIGS. 1A-1C are schematic diagrams depicting the arrangement of a series of tagged promoter oligonucleotides (e.g., promoter-primers), priming oligonucleotides (e.g., primers), and probes. Horizontal lines indicate target-hybridizing sequences of the oligonucleotides. Regions of the oligonucleotides depicted by diagonal lines represent tag sequences (shown as open boxes) and promoter sequences that do not stably hybridize to target nucleic acids under hybridizing conditions (e.g., target-capture conditions). The identities of the various nucleic acid sequences, or portions thereof, are indicated.
Figure 2A:
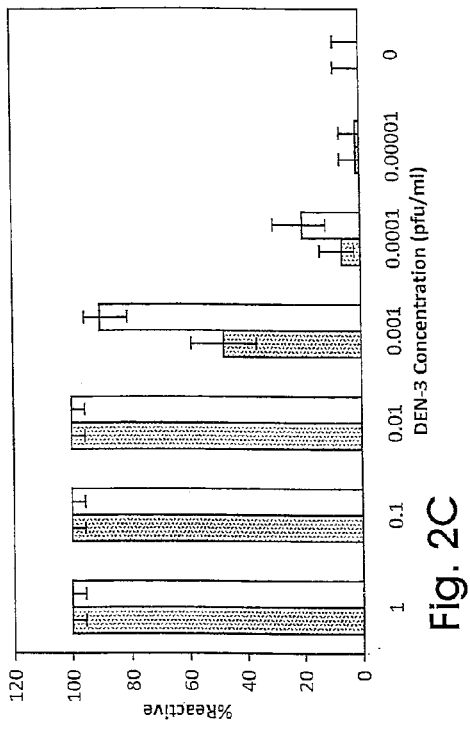
FIGS. 2A-2D are a series of bar graphs representing % reactivity as a function of Dengue virus sample concentration measured in PFU/ml (plaque forming units/ml). Results obtained using the invented 5' region assay are shown using open bars. Results obtained using a comparative 3' region assay are shown using stippled bars.
Figure 2C:
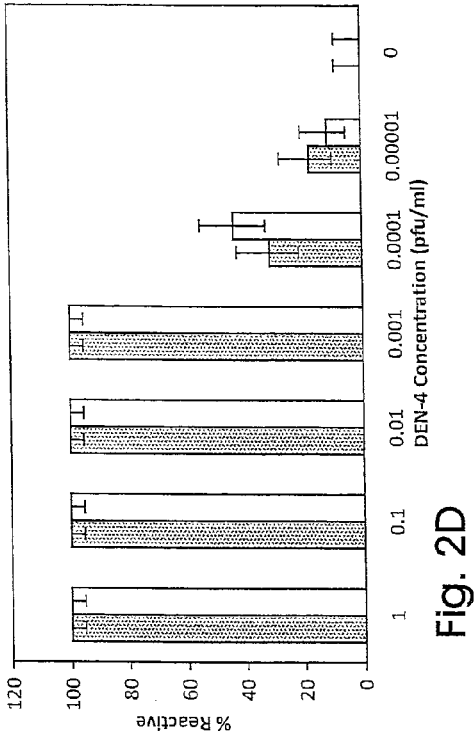
Figure 2B:
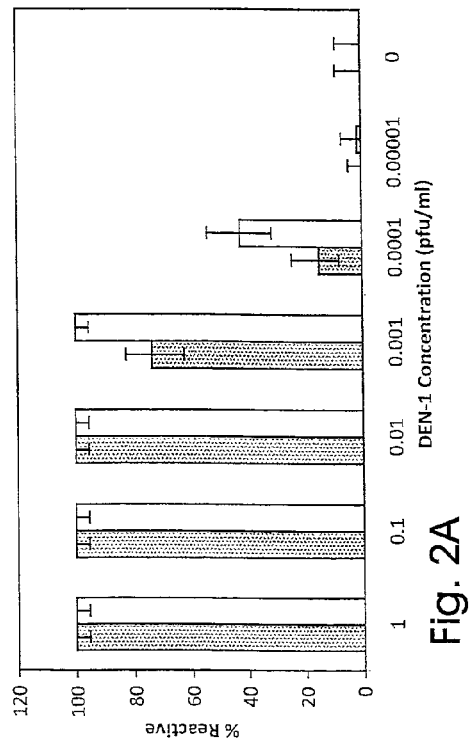
Figure 2D:
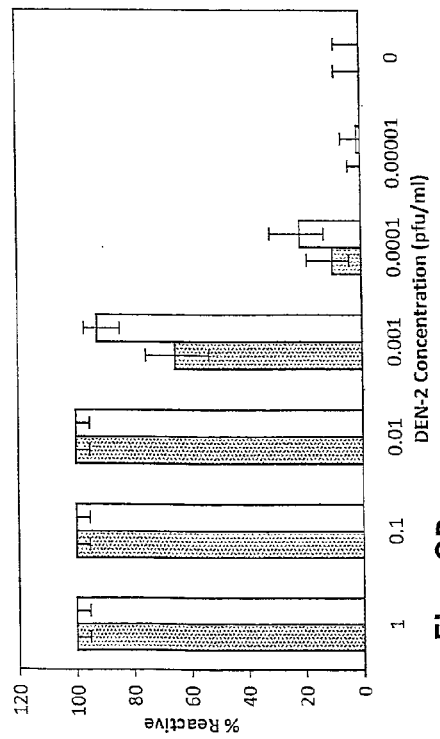

The following terms have the following meanings unless expressly stated to the contrary. It is to be noted that the term "a" or "an" entity refers to one or more of that entity. For example, "a nucleic acid," is understood to represent one or more nucleic acids. As such, the terms "a" (or "an"), "one or more," and "at least one" can be used interchangeably herein.

Nucleic Acid

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, viral genomes, or portions thereof, either DNA or RNA, or synthetic DNA or RNA. A nucleic acid may be provided in a double-stranded or single-stranded form. Nucleic acids may include modified bases to alter the function or behavior of the nucleic acid (e.g., addition of a 3'-terminal dideoxynucleotide to block additional nucleotides from being added to the nucleic acid). As used herein, the "sequence" of a nucleic acid refers to the sequence of bases which make up the nucleic acid. The term "polynucleotide" may be used herein to denote a nucleic acid chain. Throughout this application, nucleic acids are designated as having a 5'-terminus and a 3'-terminus.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "non-nucleotide unit" is a unit that does not significantly participate in hybridization of a polymer. Such units preferably do not, for example, participate in any significant hydrogen bonding with a nucleotide, and would preferably exclude units having as a component one of the five nucleotide bases or analogs thereof.

Target Nucleic Acid/Target Sequence

A "target nucleic acid" is a nucleic acid present in a nucleic acid sample comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include viral genomes.

Target nucleic acids may be isolated from any number of sources based on the purpose of the amplification assay being carried out. Sources of target nucleic acids include, but are not limited to, clinical specimens (e.g., blood, blood products such as serum or platelets, urine, saliva, feces, semen, or spinal fluid), environmental samples (e.g., water or soil samples), food samples, beverages, industrial samples (e.g., products and process materials, including water), cDNA libraries, or total cellular RNA.

By "isolated" it is meant that a sample containing a target nucleic acid is taken from its natural milieu. However, the term does not connote any particular degree of purification. If necessary, target nucleic acids of the present invention are made available for interaction with the various oligonucleotides of the present invention. This may include, for example, cell lysis or cell permeabilization to release the target nucleic acid from cells or virus particles which then may be followed by one or more purification steps, such as a series of isolation and wash steps. Useful techniques have been described by Clark et al., in "Method for Extracting Nucleic Acids from a Wide Range of Organisms," U.S. Pat. No. 5,786,208; and by Hogan in "Polynucleotide Matrix-Based Method of Identifying Microorganisms, U.S. Pat. No. 6,821,770. This may be particularly important where the sample source or cellular material released into the sample can interfere with the amplification reaction. Methods to prepare target nucleic acids from various sources for amplification are well known to those of ordinary skill in the art. Target nucleic acids of the present invention may be purified to some degree prior to the amplification reactions described herein, but in other cases, the sample is added to the amplification reaction without any further manipulations.

The term "target sequence" refers to the particular nucleotide sequence of the target nucleic acid which is to be amplified. The "target sequence" includes the complexing sequences to which oligonucleotides (e.g., tagged oligonucleotides, priming oligonucleotides and/or promoter oligonucleotides) complex during the processes of the present invention. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. A minimal target sequence includes a region which hybridizes to the target-hybridizing sequence of a tagged oligonucleotide, the complement of a region which hybridizes to a priming oligonucleotide (e.g., a primer) or the hybridizing region of a promoter oligonucleotide (e.g., a tagged promoter-primer), and a region used for detection (e.g., a region or complement thereof, which hybridizes to a detection probe, as described in more detail elsewhere herein). The region which hybridizes with the detection probe may overlap with or be contained within the region which hybridizes with the priming oligonucleotide (or its complement) or the hybridizing region of the promoter oligonucleotide (or its complement). In addition to the minimal requirements, the optimal length of a target sequence depends on a number of considerations, for example, the amount of secondary structure, or self-hybridizing regions in the sequence. Determining the optimal length is easily accomplished by those of ordinary skill in the art using routine optimization methods. The optimal or preferred length may vary under different conditions, which can easily be tested by one of ordinary skill in the art according to the methods described herein. The terms "amplicon" refers to a nucleic acid molecule generated during an amplification procedure that is substantially complementary or identical to a sequence contained within the target sequence. The term "amplification product" refers to an amplicon or some other product indicative of an amplification reaction.

In connection with oligonucleotides, the "target-hybridizing" sequence of an oligonucleotide refers to the portion or sequence of bases of the oligonucleotide that hybridizes to a target nucleic acid by complementary base pairing.

Oligonucleotides

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions. For example, it may function as a primer if it is capable of hybridizing to a complementary strand and can further be extended in the presence of a nucleic acid polymerase. It may provide a promoter if it contains a sequence recognized by an RNA polymerase and allows for transcription, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction.

Oligonucleotides of a defined sequence and chemical structure may be produced by techniques known to those of ordinary skill in the art, such as by chemical or biochemical synthesis, and by in vitro or in vivo expression from recombinant nucleic acid molecules (e.g., bacterial or viral vectors). As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine and inosine. The sugar groups of the nucleoside subunits may be ribose, deoxyribose and analogs thereof, including, for example, ribonucleosides having a 2'-O-methyl (2'-O-ME) substitution to the ribofuranosyl moiety (see Becker et al., "Method for Amplifying Target Nucleic Acids Using Modified Primers," U.S. Pat. No. 6,130,038). Other sugar modifications include, but are not limited to 2'-amino, 2'-fluoro, (L)-alpha-threofuranosyl, and pentopuranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. Notably, DNA analogs having a pseudo peptide backbone are commonly referred to as "peptide nucleic acids" or "PNA" and are disclosed by Nielsen et al., "Peptide Nucleic Acids," U.S. Pat. No. 5,539,082. Other linkage modifications include, but are not limited to, morpholino bonds.

Non-limiting examples of oligonucleotides or oligomers contemplated by the present invention include nucleic acid analogs containing bicyclic and tricyclic nucleoside and nucleotide analogs (LNAs). Any nucleic acid analog is contemplated by the present invention provided the modified oligonucleotide can perform its intended function (e.g., hybridize to a target nucleic acid under hybridization or amplification conditions, or interact with a DNA or RNA polymerase, thereby initiating extension or transcription). In the case of detection probes, the modified oligonucleotides must also be capable of preferentially hybridizing to the target nucleic acid under hybridization conditions, such as those described herein.

While the design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design.

As used in this disclosure, the phrase "an oligonucleotide having a nucleic acid sequence 'comprising,' 'consisting of,' or 'consisting essentially of' a sequence selected from" a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "an oligonucleotide substantially corresponding to" a nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that "substantially corresponding" oligonucleotides of the invention can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

Tagged Oligonucleotide/Heterologous Tag Sequence

A "tagged oligonucleotide" as used herein refers to an oligonucleotide that comprises at least a first region and a second region, where the first region comprises a "target-hybridizing sequence" which hybridizes to a target nucleic acid sequence of interest, and where the second region comprises a "tag sequence" situated 5' to the target-hybridizing sequence and which does not stably hybridize or bind to a target nucleic acid containing the target nucleic acid sequence. Hybridization of the target-hybridizing sequence to the target nucleic acid sequence produces a "tagged target nucleic acid sequence." The features and design considerations for the target-hybridizing sequence component would be the same as for the priming oligonucleotides. Because the upstream tag sequence is not essential for all amplification techniques, the tag sequence is considered optional in many applications.

The "tag sequence" or "heterologous tag sequence" may be essentially any heterologous sequence provided that it does not stably hybridize to the target nucleic acid sequence of interest and, thereby, participate in detectable amplification in the absence of a downstream target-hybridizing sequence. The tag sequence preferably does not stably hybridize to any sequence derived from the genome of an organism being tested or, more particularly, to any target nucleic acid under reaction conditions. A tag sequence that is present in a tagged oligonucleotide is preferably designed so as not to substantially impair or interfere with the ability of the target-hybridizing sequence to hybridize to its target sequence. Moreover, the tag sequence will be of sufficient length and composition such that once a complement of the tag sequence has been incorporated into an initial DNA primer extension product, a tag-specific priming oligonucleotide can then be used to participate in subsequent rounds of amplification as described herein. A tag sequence of the present invention is typically at least 10 nucleotides in length, and may extend up to 15, 20, 25, 30, 35, 40, 50 or more nucleotides in length. Skilled artisans will recognize that the design of tag sequences and tagged oligonucleotides for use in the present invention can follow any of a number of suitable strategies, while still achieving the objectives and advantages described herein.

In certain embodiments, the tagged oligonucleotide is a "tagged priming oligonucleotide" comprising a tag sequence and a target-hybridizing sequence. In other embodiments, the tagged oligonucleotide is a "tagged promoter oligonucleotide" comprising a 3' target-hybridizing sequence, a tag sequence joined upstream of the target-hybridizing sequence, and a promoter sequence joined 5' to the tag sequence and effective for initiating transcription therefrom. A tagged promoter oligonucleotide having a 3'-end that can be extended by a DNA polymerase (e.g., a reverse transcriptase) in a template-dependent fashion may be referred to as a "tagged promoter-primer."

Inactivating

The term "inactivating" means that a heterologous tagged oligonucleotide is altered so that it does not stably bind to a target nucleic acid sequence under amplification conditions. In the case of an unhybridized tagged oligonucleotide, the term "inactivating" means that the tagged oligonucleotide is altered from an "active" confirmation which permits the target-hybridizing sequence to hybridize to the target nucleic acid sequence to an "inactive" confirmation which blocks or otherwise prevents the target-hybridizing sequence from hybridizing to the target nucleic acid sequence.

Removing

As used herein, the term "removing" refers to the physical separation of tagged target nucleic acid sequences from unhybridized tagged oligonucleotides. Tagged target nucleic acid sequences can be physically separated from unhybridized tagged oligonucleotides (or heterologous tag sequences) present in a nucleic acid sample by a variety of techniques known to those skilled in the art. By way of example, tagged target nucleic acid sequences can be bound to a solid support and immobilized in a nucleic acid sample while unbound material is removed. To remove unbound material, the solid support can be subjected to one or more wash/rinse steps. The wash steps are intended to remove remaining unhybridized tagged oligonucleotides and potentially interfering cellular or sample material. A rinse step is typically included where the wash solution contains a component that is inhibitory to amplification when present at a sufficiently high concentration, such as a detergent. The solid support preferably binds specifically to target nucleic acids or tagged target nucleic acid sequences to prevent unhybridized tagged oligonucleotide (or unbound heterologous tag sequences) from entering into the amplification reaction. Exemplary means for capturing, immobilizing and purifying target nucleic acids are discussed below, an example of which is disclosed by Weisburg et al., "Two-Step Hybridization and Capture of a Polynucleotide," U.S. Pat. No. 6,534,273.

Amplification or Nucleic Acid Amplification

By "amplification" or "nucleic acid amplification" is meant production of multiple copies of a target nucleic acid that contains at least a portion of the intended specific target nucleic acid sequence. The multiple copies may be referred to as amplicons or amplification products. In certain embodiments, the amplified target contains less than the complete target gene sequence. For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (Mullis et al., U.S. Pat. No. 4,683,195; Mullis, U.S. Pat. No. 4,683,202; and Mullis et al., U.S. Pat. No. 4,800,159), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (Gelfand et al., "Reverse Transcription with Thermostable DNA Polymerases—High Temperature Reverse Transcription," U.S. Pat. Nos. 5,322,770 and 5,310,652). Another method is strand displacement amplification (Walker, G. et al. (1992), *Proc. Natl. Acad. Sci. USA* 89, 392-396; Walker et al., "Nucleic Acid Target Generation," U.S. Pat. No. 5,270,184; Walker, "Strand Displacment Amplification," U.S. Pat. No. 5,455,166; and Walker et al. (1992) *Nucleic Acids Research* 20, 1691-1696), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (Malek et al., U.S. Pat. No. 5,130,238), commonly referred to as NASBA; one that uses an RNA replicase to amplify the probe molecule itself (Lizardi, P. et al. (1988) *BioTechnol.* 6, 1197-1202), commonly referred to as Qβ replicase; a transcription-based amplification method (Kwoh, D. et al. (1989) *Proc. Natl. Acad. Sci. USA* 86, 1173-1177); self-sustained sequence replication (Guatelli, J. et al. (1990) *Proc. Natl. Acad. Sci. USA* 87, 1874-1878; Landgren (1993) *Trends in Genetics* 9, 199-202; and Lee, H. et al., NUCLEIC ACID AMPLIFICATION TECHNOLOGIES (1997)); and, transcription-mediated amplification (Kacian et al., "Nucleic Acid Sequence Amplification Methods," U.S. Pat. No. 5,480,784; and Kacian et al., U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.). Other illustrative amplification methods suitable for use in accordance with the present invention include rolling circle amplification (RCA) (Lizardi, "Rolling Circle Replication Reporter Systems," U.S. Pat. No. 5,854,033); Helicase Dependent Amplification (HDA) (Kong et al., "Helicase Dependent Amplification Nucleic Acids," U.S. Pat. Appln. Pub. No. US 2004-0058378 A1); and Loop-Mediated Isothermal Amplification (LAMP) (Notomi et al., "Process for Synthesizing Nucleic Acid," U.S. Pat. No. 6,410,278).

Preferred transcription-based amplification systems of the present invention include TMA, which employs an RNA polymerase to produce multiple RNA transcripts of a target region (e.g., Kacian et al., U.S. Pat. Nos. 5,480,784 and 5,399, 491; and Becker et al., "Single-Primer Nucleic Acid Amplification Methods," U.S. Pat. Appln. Pub. No. US 2006-0046265 A1). Transcription mediated amplification (TMA) uses a "promoter oligonucleotide" or "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA:DNA hybrid, thereby making the DNA strand available for hybridization with a primer or promoter-primer.

In one illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNAse H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNAse H activity degrades the RNA of this RNA:DNA duplex. The promoter-primer can then bind to the newly synthesized DNA, allowing the reverse transcriptase to create a double-stranded DNA, from which the RNA polymerase produces multiple amplicons.

Amplification Conditions

By "amplification conditions" is meant conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention hybridize under stringent hybridization conditions. While the Examples section infra provides preferred amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and either T or U) or cytosine and guanine (C and G) on single nucleic acid strands, base pairing can also form between bases which are not members of these "canonical" pairs. Non-canonical base pairing is well-known in the art.

"Stringent hybridization conditions" or "stringent conditions" refer to conditions where a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

By "nucleic acid hybrid" or "hybrid" or "duplex" is meant a nucleic acid structure containing a double-stranded, hydrogen-bonded region where each strand is complementary to the other, and where the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable, double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T, and C is paired with G, the nucleotides sequences are "perfectly" complementary.

By "preferentially hybridize" is meant that under stringent hybridization conditions, certain complementary nucleotides or nucleobase sequences hybridize to form a stable hybrid preferentially over other, less stable duplexes. By "does not stably hybridize" is meant that a stable hybrid is not formed in appreciable and/or detectable amounts under a defined set of conditions.

By "stable" or "stably hybridize" or "stable for detection" is meant that the temperature of a reaction mixture is at least 2° C. below the melting temperature of a nucleic acid duplex. An oligonucleotide bound to a target sequence in a manner stable for detection may be detected, for example, either by using a detectable label or by participating as a primer in an amplification reaction.

Promoter Oligonucleotide/Promoter Sequence

As is well known in the art, a "promoter" is a specific nucleic acid sequence that is recognized by a DNA-dependent RNA polymerase as a signal to bind to the nucleic acid and begin the transcription of RNA at a specific site. When an RNA polymerase binds to a promoter sequence to initiate transcription, that promoter sequence is not part of the sequence transcribed. Thus, the RNA transcripts produced thereby will not include that sequence.

According to the present invention, a "promoter oligonucleotide" refers to an oligonucleotide comprising first and second regions. The "first region" of a promoter oligonucleotide of the present invention comprises a base sequence which hybridizes to a nucleic acid template, where the hybridizing sequence is situated 3', but not necessarily adjacent to, a promoter region. The hybridizing portion of a promoter oligonucleotide of the present invention is typically at least 10 nucleotides in length, and may extend up to 15, 20, 25, 30, 35, 40, 50 or more nucleotides in length. The "second region" comprises a promoter for an RNA polymerase.

Universal Oligonucleotides

"Universal" oligonucleotides include oligonucleotides that can be used in an amplification reaction to identify the presence of nucleic acid sequences within a group of related or unrelated target sequences. Essentially any universal oligonucleotides known or developed for a given class of organism may be advantageously employed in the methods described herein.

Priming Oligonucleotide

A priming oligonucleotide is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. A priming oligonucleotide is extended by the addition of covalently bonded nucleotide bases to its 3'-terminus, which bases are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template to initiate DNA synthesis, whereas transcription (copying of RNA from DNA) generally does not proceed by extension of a primer. By its very nature of being extended by a DNA polymerase, a priming oligonucleotide does not comprise a 3'-blocking moiety. A priming oligonucleotide that includes a promoter sequence may be referred to as a "promoter-primer." Neither upstream promoter sequences nor upstream tag sequences are required of priming oligonucleotides employed in amplification methods such as PCR.

Target Capture

Target capture, as used herein, includes any technique effective to remove all or substantially all unhybridized tagged oligonucleotide after hybridization of tagged oligonucleotide with a target nucleic acid sequence but prior to amplification of the target nucleic acid sequence. Generally, target capture involves capturing a target polynucleotide onto a solid support, such as magnetically attractable particles, where the solid support retains the target polynucleotide during one or more washing steps of the target polynucleotide purification procedure. In this way, a target polynucleotide can be substantially purified from unhybridized tagged oligonucleotide prior to a subsequent nucleic acid amplification step. Numerous target capture methods are known and suitable for use in conjunction with the methods described herein.

For example, one illustrative approach described in U.S. Pat. Appln. Pub. No. US 2006-0068417 A1 uses at least one capture probe oligonucleotide that contains a target-complementary region and a member of a specific binding pair that joins a target nucleic acid to an immobilized probe on a capture support, thus forming a capture hybrid that is separated from other sample components of a sample. In another illustrative method, Weisburg et al., in U.S. Pat. No. 6,110,678, describe a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide.

Another illustrative target capture technique involves a hybridization sandwich technique for capturing and for detecting the presence of a target polynucleotide. See Ranki et al., "Detection of Microbial Nucleic Acids By a One-Step Sandwich Hybridization Test," U.S. Pat. No. 4,486,539. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Another illustrative target capture technique involves a method that uses a mediator polynucleotide that hybridizes to both a target polynucleotide and to a polynucleotide fixed on a solid support. See Stabinsky, "Methods and Kits for Performing Nucleic Acid Hybridization Assays," U.S. Pat. No. 4,751,177. The mediator polynucleotide joins the target polynucleotide to the solid support to produce a bound target. A labeled probe can be hybridized to the bound target and unbound labeled probe can be washed away from the solid support.

Yet another illustrative target capture technique is disclosed by Englehardt, "Capture Sandwich Hybridization Method and Composition," U.S. Pat. No. 5,288,609, which describes a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, methods and kits for detecting nucleic acids use oligonucleotide primers labeled with specific binding partners to immobilize primers and primer extension products. See Burdick et al., "Diagnostic Kit and Method Using a Solid Phase Capture Means for Detecting Nucleic Acids," European Pat. Appln. No. 0 370 694 A2. The label specifically complexes with its receptor which is bound to a solid support.

The above capture techniques are illustrative only, and not limiting. Indeed, essentially any technique available to the skilled artisan may be used provided it is effective for removing all or substantially all unhybridized tagged oligonucleotide after hybridization of tagged oligonucleotide with a target nucleic acid sequence but prior to amplification of the target nucleic acid sequence, as described herein.

Probe

By "probe" or "detection probe" is meant a molecule comprising an oligonucleotide having a base sequence partly or completely complementary to a region of a target sequence sought to be detected, so as to hybridize thereto under hybridization conditions, such as those disclosed herein. As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent).

The probes of this invention may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Probes may also include interacting labels which emit different signals, depending on whether the probes have hybridized to target sequences. Examples of interacting labels include enzyme/substrates, enzyme/cofactor, luminescent/quencher, luminescent/adduct, dye dimers, and Förrester energy transfer pairs. Certain probes of the present invention do not include a label. For example, non-labeled "capture" probes may be used to enrich for target sequences or replicates thereof, which may then be detected by a second "detection" probe. See, e.g., Weisburg et al., U.S. Pat. No. 6,534,273. While detection probes are typically labeled, certain detection technologies that will be familiar to those having an ordinary level of skill in the art do not require that the probe be labeled.

By "preferentially hybridize" is meant that under specified hybridization conditions, probes of the present invention hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 17 to 35 bases in length.

Template

A "template" is a nucleic acid molecule that can be copied by a nucleic acid polymerase. A template may be single-stranded, double-stranded or partially double-stranded, depending on the polymerase. The synthesized copy is complementary to the template or to at least one strand of a double-stranded or partially double-stranded template. Both RNA and DNA are typically synthesized in the 5'-to-3' direction and the two strands of a nucleic acid duplex are aligned so that the 5'-termini of the two strands are at opposite ends of the duplex (and, by necessity, so then are the 3'-termini). While according to the present invention, a "target sequence" is always a "template," templates can also include secondary primer extension products and amplification products.

DNA-Dependent DNA Polymerase

A "DNA-dependent DNA polymerase" is an enzyme that synthesizes a complementary DNA copy from a DNA template. Examples are Taq DNA polymerase, a highly thermostable DNA polymerase from the thermophilic bacterium *Therms aquaticus*, for PCR amplification reactions, DNA polymerase I from *E. coli*, bacteriophage T7 DNA polymerase, or DNA polymerases from bacteriophages T4, Phi-29, M2, or T5. DNA-dependent DNA polymerases of the present invention may be the naturally occurring enzymes isolated from bacteria or bacteriophages or expressed recombinantly, or may be modified or "evolved" forms which have been engineered to possess certain desirable characteristics (e.g., thermostability, or the ability to recognize or synthesize a DNA strand from various modified templates). All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described below) typically also have DNA-dependent DNA polymerase activity.

An example of such a polymerase is the MasterAmp™ Tth DNA Polymerase, which has both DNA-dependent and RNA-dependent (i.e., reverse transcriptase) DNA polymerase activities that can be used in both PCR and RT-PCR amplification reactions (Epicentre Biotechnologies; Madison, Wis.).

DNA-Dependent RNA Polymerase

A "DNA-dependent RNA polymerase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of preferred DNA-dependent RNA polymerase include those from the bacteriophages T7, T3, and SP6.

RNA-Dependent DNA Polymerase (Reverse Transcriptase)

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. Preferred is reverse transcriptase derived from Maloney murine leukemia virus (MMLV-RT). A primer is required to initiate synthesis with both RNA and DNA templates.

Specificity of the System

The term "specificity," in the context of an amplification system, is used herein to refer to the characteristic of an amplification system which describes its ability to distinguish between target and non-target sequences dependent on sequence and assay conditions. In terms of a nucleic acid amplification, specificity generally refers to the ratio of the number of specific amplicons produced to the number of side-products (i.e., the signal-to-noise ratio).

Sensitivity

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction.

An advantage of the present invention is the ability to detect each of Dengue virus serotypes 1-4 when the amounts of the different serotypes are similar, and low (e.g., each being present at 50, or even 20 copies/ml in a sample undergoing testing). There are alternative ways of referring to assay "sensitivity" herein, where those alternatives can be equivalent. More specifically, by convention, test samples employed herein consisted of 0.5 ml (i.e., 500 µl) from which nucleic acids were isolated. The isolated nucleic acids were then used as templates in in vitro nucleic acid amplification reactions having volumes of 100 µl. Thus, an assay conducted in a reaction volume of 100 µl that detected 10 copies of a Dengue virus nucleic acid isolated from a 0.5 ml test sample would have been capable of detecting Dengue virus nucleic acid at a concentration of 20 copies/ml in the test sample (i.e., 10 copies/0.5 ml=20 copies/ml).

Introduction and Overview

Herein there are described various compositions and methods useful for amplifying and detecting nucleic acids of the four different Dengue virus serotypes with substantially similar sensitivities. This is important because the different viral genotypes exhibit relatively limited nucleic acid sequence conservation, thereby rendering efficient coamplification and detection difficult, as confirmed by the prior attempts of others. By following the disclosed methods, it is now possible to detect nucleic acids of all four Dengue virus serotypes with substantially equivalent sensitivity down to about 45 copies/ml, and even down to 20 copies/ml of the different nucleic acid targets.

Oligonucleotide Reagents

The disclosed assays employ a number of oligonucleotides which may serve as hybridization detection probes; tagged promoter oligonucleotides (e.g., promoter-primers); priming oligonucleotides (e.g., primers); etc. Since all of the disclosed oligonucleotides interact with at least one other nucleic acid through complementary base pairing, each of the disclosed oligonucleotides includes a target-hybridizing sequence of bases. FIGS. 1A-1C show the arrangement of various oligonucleotides that can be used in the detection of nucleic acids for all of Dengue virus serotypes 1-4.

FIG. 1A illustrates an amplification and detection system that employs a number of the oligonucleotides disclosed herein. In this instance the combination of first-strand primers having the target-hybridizing sequences of SEQ ID NO: 10 and SEQ ID NO: 1 contact a Dengue virus template nucleic acid (i.e., any of serotypes 1-4) and serve as primers in the presence of a DNA polymerizing enzyme (e.g., reverse transcriptase) to create primer extension products (e.g., cDNA). Notably, both of these first-strand primers are illustrated to include at their 5'-ends a tagged promoter sequence (e.g., SEQ ID NO: 26) that does not stably hybridize to any of the Dengue virus serotype 1-4 nucleic acids in the absence of the target-hybridizing sequences provided by SEQ ID NO: 10 or SEQ ID NO: 1. Use of the tag sequence is optional in standard TMA amplification reactions, as disclosed by Kacian et al., in U.S. Pat. Nos. 5,480,784 and 5,399,491, but is essential in the modified amplification technique disclosed by Becker et al., in U.S. Ser. No. 11/810,834 (entitled "Tagged Oligonucleotides and Their Use in Nucleic Acid Amplification Methods"). The primer extension products can hybridize to at least one opposite-strand primer having target-hybridizing sequences given by SEQ ID NO: 16 and/or SEQ ID NO: 13. The opposite-strand primer(s) can then be extended using the cDNA strand as a template to result in a double-stranded amplification product. As will be apparent from the diagram in FIG. 1B and the results presented under Example 3, use of a primer having the target-hybridizing sequence of SEQ ID NO: 16 is optional. If the double-stranded amplification products include a promoter sequence, then RNA amplification products also can be synthesized. Dengue-specific amplification products can stably hybridize to an oligonucleotide probe having a target-hybridizing sequence conforming to the sequence of SEQ ID NO: 19, or the complement thereof.

FIG. 1B illustrates a simplified amplification and detection system that employs a subset of the oligonucleotides diagramed in FIG. 1A. In the simplified system a first-strand primer having the target-hybridizing sequence of SEQ ID NO: 1 contacts a Dengue virus template nucleic acid (i.e., any of serotypes 1-4) and serves as a primer in the presence of a DNA polymerizing enzyme (e.g., reverse transcriptase) to create primer extension products (e.g., cDNA). Notably, the first-strand primer is illustrated as including at its 5'-end a tagged promoter sequence (e.g., SEQ ID NO: 26) that does not stably hybridize to any of the Dengue virus serotype 1-4 nucleic acids in the absence of the target-hybridizing sequence provided by SEQ ID NO: 1. The primer extension products can hybridize to an opposite-strand primer having the target-hybridizing sequence given by SEQ ID NO: 13. The opposite-strand primer can then be extended using the cDNA strand as a template to result in double-stranded amplification products. If the double-stranded amplification products include a promoter sequence, then RNA amplification products also can be synthesized. Dengue-specific amplification products can stably hybridize to an oligonucleotide probe having a target-hybridizing sequence conforming to the sequence of SEQ ID NO: 19, or the complement thereof.

FIG. 1C illustrates yet another simplified amplification and detection system. In this instance, a first-strand primer having the target-hybridizing sequence of SEQ ID NO: 1 contacts a Dengue virus template nucleic acid (i.e., any of serotypes 1-4) and serves as a primer in the presence of a DNA polymerizing enzyme (e.g., reverse transcriptase) to create primer extension products (e.g., cDNA). Notably, the first-strand primer is illustrated as including at its 5'-end a tagged promoter sequence (e.g., SEQ ID NO: 26) that does not stably hybridize to any of the Dengue virus serotype 1-4 nucleic acids in the absence of the target-hybridizing sequence provided by SEQ ID NO: 1. The primer extension products can hybridize to an opposite-strand primer having a target-hybridizing sequence that conforms to the sequence of SEQ ID NO: 19. The opposite-strand primer can then be extended using the cDNA strand as a template to result in a double-stranded amplification product. Subsequent rounds of amplification can employ as a primer the same tagged promoter-primer sequence (e.g., SEQ ID NO: 26) that was used upstream of the target-hybridizing sequence of the first-strand promoter-primer. If the double-stranded amplification products include a promoter sequence, then RNA amplification products also can be synthesized. Dengue-specific amplification products can stably hybridize to an oligonucleotide probe having a target-hybridizing sequence of SEQ ID NO: 25, or the complement thereof.

Table 1 presents the sequences of certain highly preferred oligonucleotides used for amplifying and detecting Dengue virus nucleic acids. Although it is allowed that oligonucleotides of the invention may serve alternative functions, particularly preferred functions of the oligonucleotides are listed in the table.

TABLE 1

Oligonucleotide Sequences

| Function | Sequence | Identifier |
|---|---|---|
| target-hybridizing sequence of primer | CGGTTTCTCNCGCGT TTCAGCATATTGA | SEQ ID NO: 1 |
| target-hybridizing sequence of primer | CGGTTTCTCNCGCGT TTCAGCAT | SEQ ID NO: 10 |
| target-hybridizing sequence of primer | GCTTAACRYAGTTCT RACAGTT | SEQ ID NO: 13 |
| target-hybridizing sequence of primer | GGACCGACAAGRACA G | SEQ ID NO: 16 |
| target-hybridizing sequence of primer or probe | TAGAGAGCAGATNTC TG | SEQ ID NO: 19 |
| target-hybridizing sequence of probe | UCAAUAUGCUGAAAC GCG | SEQ ID NO: 25 |
| tagged promoter sequence | AATTTAATACGACTC ACTATAGGGAGATAT GAATGCGACCCGGAA | SEQ ID NO: 26 |

In a preferred embodiment of the invention, there is an oligonucleotide that contains a target-hybridizing sequence which can be used, in full or in part, as a probe or a primer in relative orientations opposite to each other. The target-hybridizing sequence of a particularly preferred primer orientation is given by SEQ ID NO: 1. Position 10 of this sequence is preferably occupied by any of G, T/U, A or C; or more preferably occupied by any of G, T/U or A to result in an oligonucleotide exactly complementary to at least one of the in vitro transcripts employed in the procedures disclosed herein. Alternatively, position 10 can be occupied by a nucleotide base analog, such as I (inosine). An exact match to the complementary base at this position in the target nucleic acid undergoing amplification is not believed critical for success, and so several instances of priming oligonucleotides containing inosine were used for demonstration purposes (i.e., not an exact complement to any particular base). For example, SEQ ID NO: 2 presents the target-hybridizing sequence of an oligonucleotide having inosine substituted at position 10. When used as a primer, the oligonucleotide optionally may include an upstream promoter for a phage RNA polymerase (e.g., SEQ ID NO: 28), and the primer can be used as a promoter-primer. The promoter-primer may further include an optional sequence interposed between the target-hybridizing sequence and the upstream promoter. The interposed sequence may serve as a tag sequence that can be used during a target capture step, or an amplification step, if desired. An example of a promoter-primer configured to include an example tag sequence (e.g., SEQ ID NO: 27) is given by the sequence of SEQ ID NO: 3. Notably, certain preferred amplification reactions in accordance with the invention contain a first-strand primer having a target-hybridizing sequence of SEQ ID NO: 1, either alone or in combination with a first-strand primer having a target-hybridizing sequence of SEQ ID NO: 10. Indeed, during the development of the invention identical results were achieved using primers having these target-hybridizing sequences individually and in combination.

A slightly shorter first-strand primer had a target-hybridizing sequence fully contained within the sequence of SEQ ID NO: 1, described immediately above. More particularly, the target-hybridizing sequence of another preferred primer is given by SEQ ID NO: 10. As above, position 10 is preferably occupied by any of G, T/U, A or C; or more preferably occupied by any of G, T/U or A, to result in an oligonucleotide exactly complementary to at least one of the in vitro transcripts employed in the procedures disclosed herein. Alternatively, position 10 can be occupied by a nucleotide base analog, such as I (inosine). An exact match to the complementary base at this position in the target nucleic acid undergoing amplification is not believed critical for success, and so several instances of priming oligonucleotides containing inosine were used for demonstration purposes (i.e., not an exact complement to any particular base). For example, SEQ ID NO: 11 presents the target-complementary sequence of an oligonucleotide having inosine substituted at position 10. As indicated above, oligonucleotide primers can include one of these target-complementary sequences joined to an upstream promoter sequence to result in a promoter-primer. Again, there can be an optional intervening tag sequence present in the promoter-primer between the target complementary sequence and the promoter. An example promoter-primer having this configuration is given by the sequence of SEQ ID NO: 12. As indicated above, preferred amplification reactions contain a first-strand primer having a target-hybridizing sequence of SEQ ID NO: 10, either alone or in combination with a first-strand primer having a target-hybridizing sequence of SEQ ID NO: 1. Indeed, identical results were achieved using primers having these target-hybridizing sequences individually and in combination, as indicated above.

In a preferred embodiment of the invention, there is an oligonucleotide conforming to the sequence of SEQ ID NO: 13. This opposite-strand primer is preferably used in combination with a primer that includes the sequence of SEQ ID NO: 10 (e.g., SEQ ID NO: 1) to perform a nucleic acid amplification reaction using as the template any of Dengue virus serotypes 1-4. Indeed, the primer of SEQ ID NO: 13 can be used in combination with either or both primers having the target-hybridizing sequences of SEQ ID NO: 1 and SEQ ID NO: 10, as these latter primers are redundant. Example 3, below, demonstrates an exemplary amplification reaction performed using this oligonucleotide combination.

Yet another preferred primer conforms to the sequence of SEQ ID NO: 16. As indicated above in connection with the discussion of the primer containing the target-hybridizing sequence of SEQ ID NO: 13, the primer of SEQ ID NO: 16 is preferably used in combination with a primer that includes the sequence of SEQ ID NO: 10 (e.g., SEQ ID NO: 1) to perform a nucleic acid amplification reaction using as the template any of Dengue virus serotypes 1-4. In a highly preferred embodiment of the invention, the redundant primers of SEQ ID NO: 16 and SEQ ID NO: 13 are used together. Examples 1-2, below, demonstrate exemplary amplification reactions performed using these oligonucleotides in combination.

In a preferred embodiment of the invention, there is an oligonucleotide that includes a sequence of bases useful as either a probe or a primer, wherein the probe or primer optionally includes substitution of a conventional base at one position for a different conventional base, or substitution of a base analog for a conventional base at that same position. Variants of RNA and DNA equivalent bases (e.g., substitution of T for U, and vice versa) in the sequence of bases are considered generally equivalent, and so fall outside the substitution guidance. For example, a preferred oligonucleotide has the sequence of SEQ ID NO: 19, where position 13 is occupied by either Y (pyrimidine) or I (inosine). An oligonucleotide having a C residue at position 13 (i.e., SEQ ID NO: 20) exactly matches the sequence (allowing for substitution of RNA and DNA equivalent bases) found in the in vitro transcripts employed in the procedures disclosed herein. An equivalent sequence having T residues substituted by U residues (i.e., SEQ ID NO: 22) was demonstrated for use as a probe. To demonstrate that a conventional nucleotide can be substituted into the sequence, a U residue was substituted for the C residue at position 13 to yield the sequence of SEQ ID NO: 23, and the resulting oligonucleotide used as a probe. To demonstrate that a nucleotide base analog can be substituted into the oligonucleotide sequence, an oligonucleotide having the sequence of SEQ ID NO: 21, which included I (inosine) substituted for the C residue at position 13, was employed as a primer. Accordingly, the invention embraces an oligonucleotide having the target-hybridizing sequence of SEQ ID NO: 19 (allowing for RNA and DNA equivalent base substitutions), where position 13 may be substituted by a different conventional base, or by a nucleotide base analog. Any of these oligonucleotides can be used as a probe for detecting nucleic acids of any of Dengue virus serotypes 1-4. Preferred primers have DNA backbones, and preferably have T residues in place of U residues.

Internal Control Systems for Monitoring Reaction Integrity

Some of the procedures described below incorporated an optional internal control to verify reaction validity. In these instances, an internal control nucleic acid (e.g., an RNA template) co-amplified with the Dengue virus analyte nucleic acid in the amplification reaction mixtures. The internal control amplification product and the Dengue virus analyte amplification product were detected independently. Two different internal control systems were employed in the procedures described below.

A first arrangement for internal control systems was useful for monitoring the integrity of amplification and detection reactions that employ paired sets of primers and an oligonucleotide probe that hybridized amplification product at a position between the primer binding sites, or the complements thereof. This arrangement was used in the assays described under Examples 1-3, below. In a simple application, the internal control template nucleic acid can be distinguished from the analyte template nucleic acid at the sequence of bases serving as the probe binding site. These bases may be scrambled, replaced by an unrelated base sequence, or simply contain a sufficient number of point mutations to result in differential probe binding. In this way, nucleic acid products resulting from amplification of analyte nucleic acid can be detected by an analyte-specific probe, and not by an internal control-specific probe Likewise, amplicons resulting from amplification of internal control nucleic acid can be detected by an internal control-specific probe, and not by an analyte-specific probe. This configuration allows that both analyte and internal control nucleic acid templates may be amplified using identical primers, or primer sets.

Preferred amplification reactions based on the mechanism illustrated under Example 4 include an internal control template nucleic acid that co-amplifies with analyte nucleic acid using one unique primer and one shared primer. Use of the unique primer results in an amplification product distinguishable from analyte amplicons based on the sequences used for probe binding. Because the procedure described under Example 4 employed only two oligonucleotide binding regions of the template for both amplification and detection, the internal control template differs in sequence from analyte nucleic acid at the sequence complementary to the target-hybridizing portion of the tagged promoter oligonucleotide (e.g., tagged promoter-primer). Thus, internal control amplification reactions preferably are initiated using an internal control-specific tagged promoter oligonucleotide that includes a target-hybridizing sequence complementary to the internal control template, but not complementary to any analyte template nucleic acid. This facilitates amplification of the internal control using the internal control-specific tagged promoter oligonucleotide and not the analyte-specific tagged promoter oligonucleotide. Likewise, this facilitates amplification of analyte nucleic acids using the analyte-specific tagged promoter oligonucleotide and not the internal control-specific tagged promoter oligonucleotide. Preferably, both the analyte nucleic acid and internal control template nucleic acid can be amplified using a shared primer, such as a priming oligonucleotide that hybridizes to the extension products of the tagged promoter oligonucleotide using control nucleic acids as templates. The probe used for detecting internal control amplification products is preferably complementary to the target-hybridizing sequence of the internal control-specific tagged promoter oligonucleotide. Notably, hybridization probes used for detecting analyte amplicons and internal control amplicons preferably are combined and used together in detection reactions. This is true whether amplification products are detected at the conclusion of an amplification reaction (e.g., endpoint detection format) or detected while the amplification reaction is occurring (e.g., real-time detection format).

Generally speaking, the structural relationship between the probe and tagged promoter oligonucleotide used in the reaction mixtures disclosed herein supports real-time monitoring of amplification reactions, and allows that amplifiable variants (e.g., related viral subtypes, or allelic variants that can be amplified using a shared tagged promoter oligonucleotide) can be detected using a single hybridization probe. Preferred hybridization probes include a sequence of bases complementary to a sequence fully contained within the target-hybridizing sequence of the tagged promoter oligonucleotide. Probes optionally may include at the 5' and/or 3' ends thereof a sequence of bases not complementary to the tagged promoter oligonucleotide or to an amplification product generated by the activity or use of that tagged promoter oligonucleotide. These non-complementary bases may be, for example, arm sequences of a molecular beacon that serve to maintain the stem structure in the absence of binding to a target nucleic acid. Alternatively, the non-complementary bases may be base positions within a molecular torch that serve to maintain secondary structure of the probe in the absence of binding to target such that the fluorophore and quencher are held in close physical relationship. Preferred probes do not form stable hybridization complexes with other sequences contained within the tagged promoter oligonucleotide under hybridization conditions provided by the amplification reaction mixture conditions described herein. Where a different approach may guide that hybridization probes should be complementary to primer sequences fully or partially outside the target-hybridizing sequence of a primer that comprises a target-hybridizing sequence downstream of a promoter sequence (with an intervening sequence therebetween), preferred embodiments of the present invention are distinct. According to these embodiments, the target-hybridizing bases of the probe are complementary only to the target-hybridizing sequence of the tagged promoter oligonucleotide, or to a sequence fully contained within the tagged promoter oligonucleotide. This simplifies the design of the oligonucleotide probe and tagged promoter oligonucleotide. In applications conducted using a real-time amplification format (i.e., with the probe being included in the reaction as amplification is taking place), it is preferred for the probe to be capable of generating an increased fluorescent signal when hybridized to a target nucleic acid when compared with unhybridized probe free in solution. Particularly preferred is a probe that includes a fluorophore, and that yields a stronger fluorescent emission when the probe is hybridized to a target nucleic acid compared to when the probe is not hybridized to a target nucleic acid. More preferably, the probe further comprises a fluorescent quencher moiety. Examples of such probes include molecular beacons, molecular torches, molecular switches, and even probes substantially lacking secondary structure, as will be familiar to those having an ordinary level of skill in the art (see U.S. Pat. No. 7,348,141). In light of the structural relationship between the oligonucleotide probe and the tagged promoter oligonucleotide (e.g., a tagged promoter-primer), the two oligonucleotides preferably do not contact each other until after completion of a step that inactivates or removes unhybridized or excess tagged promoter oligonucleotide from the amplification reaction mixture. This can be accomplished using a target capture step for isolating target nucleic acids hybridized to the tagged promoter oligonucleotide, or by the use of a hairpin tag molecule, for example as disclosed by Becker et al., in U.S. patent application publication 2007/0281317.

ILLUSTRATIVE EXAMPLES

The general principles of the present invention may be more fully appreciated by reference to the following non-limiting Examples.

The invention provides systems for amplifying and detecting, with substantially equivalent sensitivity, all of Dengue virus serotypes 1-4. In a preferred application, an assay is used for screening test samples, such as donated blood samples, to determine the presence or absence of any of Dengue virus serotypes 1-4. In another preferred application, an assay is used for diagnostic purposes. Both applications benefit from high levels of sensitivity, even without particularly identifying the serotype of the virus. Of course, as will be apparent from the information presented herein, serotype identification can be accomplished using the disclosed primers and either serotype-specific probes, or a single probe analyzed for hybrid interaction with amplicons using a probe melting curve analysis. Those having an ordinary level of skill in the art will appreciate that probe melting curves are useful for identifying amplification products and mutations. An example of melting curve analysis is presented in U.S. patent application publication 2004/0014119.

In addition to the invented assays for amplifying Dengue sequences in the 5' region of the viral genome (i.e., the "5' region" assays), there also was developed an independent model assay for amplifying and detecting Dengue virus nucleic acids in the 3' non-coding region of the viral genome (i.e., the "3' region" assay). The oligonucleotide primers and probe used in the 3' region assay were closely related to those employed by Usawattanakul et al., (see above). When compared with the amplification product synthesized in the assay described by Usawattanakul et al., the amplification product synthesized in our procedure was slightly longer. Based on the results presented below in Example 1, we estimated our 3' region assay detected live virus for each of Dengue virus serotypes 1-4 with a sensitivity approximately ten-fold greater than the gel-based assay described by Usawattanakul et al. Accordingly, our 3' region assay served as a basis for comparison during development of the assay disclosed herein, and was believed to represent a more stringent test for superior results when compared with prior art assays. The experimental results presented herein confirmed that the presently disclosed assays for detecting Dengue virus nucleic acids were still several fold more sensitive than even our 3' region assay that was an improvement over the prior art.

Procedures for amplifying Dengue sequences in the 5' region of the viral genome employed as sources of nucleic acid templates either live Dengue virus serotypes 1-4, or in vitro-synthesized transcripts having sequences corresponding to those same viral isolates. Nucleic acids isolated from the different virus samples were separately reverse transcribed, PCR amplified and then used to create plasmid clones harboring Dengue virus inserts downstream of phage promoters. Linearized plasmids and a commercially obtained phage RNA polymerase were then used for synthesizing RNA transcripts that served as templates in the amplification reactions. The in vitro transcripts employed in the procedures described herein were between about 1.5 kb and 1.7 kb in length. The sequences of the in vitro transcripts corresponding to the live Dengue virus serotypes 1-4 comprised, respectively, SEQ ID NO: 36, SEQ ID NO: 37, SEQ ID NO: 38 and SEQ ID NO: 39. Use of in vitro transcripts as templates in the procedure provided a simple, highly quantitative procedure that could be used for comparing the sensitivities of different assay formulations.

In addition to the in vitro transcripts that included authentic Dengue virus sequences, two additional in vitro transcripts were employed as internal control templates. These in vitro transcripts had the sequences of SEQ ID NO: 40 and SEQ ID NO: 41. Base positions 96-119 of SEQ ID NO: 40 represented a sequence absent from authentic Dengue virus. Base positions 150-173 of SEQ ID NO:41 represented a sequence absent from authentic Dengue virus.

Example 1 describes methods for amplifying and detecting the nucleic acids of Dengue virus serotypes 1-4. Reagents used in the procedure included oligonucleotides having target-hybridizing sequences conforming to the sequences of SEQ ID NO: 1, SEQ ID NO: 10, SEQ ID NO: 13, SEQ ID NO: 16, and SEQ ID NO: 19.

Example 1

Amplification of Dengue Virus Nucleic Acids

Amplification reactions were performed using oligonucleotides targeting either: (a) the 5' region of the Dengue virus genome in a region having only moderate sequence conservation, or (b) the 3' region of the Dengue virus genome in an assay used for comparison. Target capture oligonucleotides used for purifying nucleic acids preliminary to the amplification and detection reactions included the target-complementary sequences of SEQ ID NO: 29, SEQ ID NO: 30, SEQ ID NO: 31 and SEQ ID NO: 32, each being independently joined at it's 3'-end to a sequence of three T residues followed by 30 A residues (i.e., SEQ ID NO: 33). The target capture oligonucleotides comprising the sequences of SEQ ID NO: 29 and SEQ ID NO: 30 were included for redundancy, and were beneficial in connection with capture of templates to be amplified in the comparative 3' assay described herein. However, these redundant target capture oligonucleotides are not required for highly sensitive 5' region assays, as disclosed herein. Notably, the target capture oligonucleotide of SEQ ID NO: 32 was able, in the absence of other target capture oligonucleotides, to capture nucleic acid targets of all four of the Dengue virus serotypes using live virus samples at low input levels. Oligonucleotide primers used in the 5' region assay included the Dengue virus target-hybridizing sequences of SEQ ID NO: 2 (i.e., conforming to SEQ ID NO: 1) and SEQ ID NO: 11 (i.e., conforming to SEQ ID NO: 10) joined downstream of the optional tagged promoter primer sequence of SEQ ID NO: 26 (i.e., the full sequences being given by SEQ ID NO: 3 and SEQ ID NO: 12, respectively), together with SEQ ID NO: 17 and SEQ ID NO: 18 (i.e., both conforming to SEQ ID NO: 16), and further including SEQ ID NO: 14 and SEQ ID NO: 15 (i.e., both conforming to SEQ ID NO: 13). Detection of amplification products was by hybridization of a mixture of labeled oligonucleotide probes having the sequences of SEQ ID NO: 22 and SEQ ID NO: 23 (i.e., both conforming to SEQ ID NO: 19). The probe of SEQ ID NO: 22 was labeled with acridinium ester between nucleotide positions 5-6 or 8-9, and the probe of SEQ ID NO: 23 was labeled with acridinium ester between nucleotide positions 8-9. This illustrates flexibility in the labeling technique. Notably, amplification products were detected with good results using these probes individually. Thus, use of the probe combination is regarded as redundant and optional, with the individual probes each representing separate preferred embodiments. An internal control transcript included in each amplification reaction had the sequence of SEQ ID NO: 40. The internal control amplification product was detected using an oligonucleotide probe of SEQ ID NO: 24 that was internally labeled with acridinium ester between nucleotide positions 10-11, again illustrating flexibility in the labeling technique.

Live virus stocks obtained from cultured cells were the source of Dengue virus templates in amplification reactions that employed opposed sets of primers. Each of the four serotypes was used over a concentration range that included 1.0, 0.1, 0.001, 0.0001, 0.00001 and 0.0 PFU/ml. Nucleic acids underwent specimen processing and target capture prior to amplification essentially according to the procedures disclosed in published International Patent Application No. PCT/US2000/18685, except that templates were captured using Dengue virus target capture oligonucleotides having the sequences given above. Notably, capture oligonucleotides do not participate in the amplification or detection reactions of the assay. Virus-containing samples having volumes of 0.5 ml were combined with a target-capture reagent to facilitate nucleic acid release and hybridization to capture oligonucleotides disposed on magnetic beads. Transcription mediated amplification (TMA) reactions were carried out essentially as described by Kacian et al., in U.S. Pat. No. 5,399,491, the disclosure of this U.S. patent having been incorporated by reference hereinabove. Amplification reactions were conducted for various primer combinations using about 10 pmoles of each primer in 100 µl of reaction buffer. Isolated target nucleic acids were combined with primers in a standard nucleic acid amplification buffer, heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. Amplification reactions were carried out in a Tris-buffered solution (pH 8.2 to 8.5) containing KCl, deoxyribonucleoside 5'-triphosphates, ribonucleoside 5'-triphosphates, N-Acetyl-L-Cysteine, and 5% (w/v) glycerol, as will be familiar to those having an ordinary level of skill in the art.

After a one hour incubation at 42° C., the 100 µl amplification reaction volumes were subjected to hybridization assays employing probes prepared using 2'-Ome nucleotide analogs. Probes were labeled with acridinium ester using techniques familiar to those having an ordinary level of skill in the art, and then used in amounts equivalent to about $3.5 \times 10^6$ RLU for each probe in the hybridization reaction. Probes were each labeled with an AE moiety joined to the oligonucleotide structure by an internally disposed non-nucleotide linker according to procedures described in U.S. Pat. Nos. 5,585,481 and 5,639,604, the disclosures of these patents are incorporated by reference. Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label linked to unhybridized probe, and cooled briefly to room temperature (i.e., 15-30° C.) prior to reading the hybridization signal. Chemiluminescence due to hybridized probe in each sample was assayed using commercially available instrumentation (Gen-Probe Incorporated; San Diego, Calif.) configured for injection of 1 mM nitric acid and 0.1% (v/v) hydrogen peroxide, followed by injection of a solution containing 1 N sodium hydroxide. Results for the chemiluminescent reactions were measured in relative light units (RLU). In this procedure, the signal/noise value corresponded to the chemiluminescent signal (measured in RLU) generated by label associated with specifically hybridized probe divided by a background signal measured in the absence of a target nucleic acid. Trials were conducted using replicates of 80. Reactivity was judged using a standard signal-to-cutoff (i.e., "S/CO") analysis of the hybridization signal results. A cutoff threshold was first established by adding 3% of a positive calibrator signal and the average of the background signals for virus-negative control samples. The positive calibrator included 500 copies/ml of the Dengue virus serotype-1 in vitro transcript. Hybridization signal results for test samples were divided by the cutoff value to calculate S/CO values. Test samples yielding S/CO values greater than 1.0 were identified as virus-positive (i.e., scored as reactive).

FIGS. 2A-2D present results for percent reactivity as a function of input Dengue virus concentration for the 5' region assay, and for the comparative 3' region assay. Regression analysis using the Probit function in SAS® System software (version 9.1.3) (Cary, N.C.) was used to calculate the 95% detection levels (i.e., target concentration required for 95% probability of detection) for each serotype using the different assays. The results appearing in Table 2 confirmed that the invented 5' region assay was substantially more sensitive than the comparative 3' region assay (see last column in the table). The tabulated results further indicated that the range of sensitivities for the different serotypes was advantageously narrower for the 5' region assay. Stated differently, the 5' region assay detected the different Dengue virus serotypes with greater sensitivity, and with better uniformity than the comparative assay. Both of these points are supported by the experimental results presented under Example 2, and in FIGS. 2A-2D.

TABLE 2

Quantifying Assay Sensitivity Using Live Virus

| Target | 95% Detection (PFU/ml) | | Fold Improvement |
|---|---|---|---|
| | 3' Region Assay | 5' Region Assay | |
| Dengue-1 | 0.003290 | 0.000506 | 6.5 |
| Dengue-2 | 0.004260 | 0.001390 | 3.1 |
| Dengue-3 | 0.006490 | 0.001470 | 4.4 |
| Dengue-4 | 0.001410 | 0.000861 | 1.6 |

An important and nonobvious advantage of the 5' region assay relates to assay integrity—the ability of an assay to detect virus-positive samples correctly as a function of input target levels. FIGS. 3A-3D present S/CO values for each of the Dengue virus serotypes in reactions that yielded reactive samples. An ideal profile on these plots would appear as uniformly high bars at all levels of input target, and drop to zero in the absence of target. An assay displaying an S/CO profile that maintains relatively high values would indicate robustness, or the ability to yield a correct determination across the range of input target levels. An assay displaying a declining trend leading to S/CO values close to 1.0 would be associated with ambiguity in the assay result at the lower S/CO levels. The relative benefit of the invented 5' region assay can be appreciated by comparing the results for the 3' region and 5' region assays presented in FIG. 3C. To achieve, using the comparative 3' region assay, S/CO values characteristic of reactions performed at 0.0001 PFU/ml of DEN-3 using the invented 5' region assay, it was necessary to use between 100-1,000 fold higher target concentrations. The results presented in FIGS. 3A and 3B support a similar trend, but show it was necessary to use between 10-100 fold higher target concentrations. Thus, for reasons that would not have been apparent even from the improved sensitivity data presented in the table, the invented 5' region assay exhibited unexpected benefits when compared with the 3' region assay that similarly detected all serotypes.

Generally speaking, alternative first-strand primers had the target-hybridizing sequence of SEQ ID NO:1, where position 10 is preferably occupied by any of G, T/U, A or C; or more preferably occupied by any of G, T/U or A, or even I (inosine), where the sequence was shortened at the 3'-end by a variable number of bases. For example, the target-hybridizing sequence of SEQ ID NO:1 was shortened by 0, 1, 2, 3, 4, 5, 6, or 7 bases to yield priming oligonucleotides that all gave good results. Each of these possibilities was tested, with the individual sequences being presented in Table 3.

TABLE 3

Target-Hybridizing Sequences for Alternative First-Strand Priming Oligonucleotides

| Sequence | Identifier |
| --- | --- |
| CGGTTTCTCNCGCGTTTCAGCATATTGA | SEQ ID NO: 1 |
| CGGTTTCTCNCGCGTTTCAGCATATTG | SEQ ID NO: 42 |
| CGGTTTCTCNCGCGTTTCAGCATATT | SEQ ID NO: 43 |
| CGGTTTCTCNCGCGTTTCAGCATAT | SEQ ID NO: 44 |
| CGGTTTCTCNCGCGTTTCAGCATA | SEQ ID NO: 45 |
| CGGTTTCTCNCGCGTTTCAGCAT | SEQ ID NO: 10 |
| CGGTTTCTCNCGCGTTTCAGCA | SEQ ID NO: 46 |
| CGGTTTCTCNCGCGTTTCAGC | SEQ ID NO: 47 |

Indeed, during development of the invention it was discovered that individual first-strand promoter-primers could be used with one or more opposite-strand primers in amplification reactions to give excellent results. Moreover, it was discovered that a collection of alternative first-strand primers could be used with excellent results. Testing, which involved amplifying the above-described synthetic template of SEQ ID NO: 38 at an exceedingly low input concentration (i.e., 11 copies/ml), was conducted using various shortened primers, both as individual (i.e., lone) first-strand primers and in combination with a first-strand primer (i.e., a tagged promoter-primer) having the target-hybridizing sequence of SEQ ID NO: 2 (i.e., conforming to SEQ ID NO: 1). For example, the tagged promoter-primer having the target-hybridizing sequence of SEQ ID NO: 2 was shortened by 1 base to yield a primer having the target-hybridizing sequence of SEQ ID NO: 4 (i.e., conforming to SEQ ID NO: 42), or shortened by 5 bases to yield a primer having the target-hybridizing sequence of SEQ ID NO: 11 (i.e., conforming to SEQ ID NO: 10). Each of these three primers gave identical results when used as the only first-strand primer together with opposite-strand primers described under Example 1, or in combinations having two different first-strand primers where one of the primers had the target-hybridizing sequence of SEQ ID NO: 2. Likewise, shortening the primer comprising the target-hybridizing sequence of SEQ ID NO: 2 by 6 bases to yield a primer having the target-hybridizing sequence of SEQ ID NO: 8 (i.e., conforming to SEQ ID NO: 46), or shortening by 7 bases to yield a primer having the target-hybridizing sequence of SEQ ID NO: 9 (i.e., conforming to SEQ ID NO: 47), and then using those primers as the only first-strand primer, together with opposite-strand primers in accordance with Example 1, gave results similar to each other, with only marginally lower activity than the comparative first-strand primer comprising SEQ ID NO: 2. Again, first-strand primer combinations that included SEQ ID NO: 2 gave 100% reactivity. First-strand primers having the target-hybridizing sequences of SEQ ID NO: 5 (i.e., conforming to SEQ ID NO: 43), SEQ ID NO: 6 (i.e., conforming to SEQ ID NO: 44) and SEQ ID NO: 7 (i.e., conforming to SEQ ID NO: 45) (i.e., the primer of SEQ ID NO: 3 shortened at its 3'-end by 2-4 bases) are fully complementary (except for inosine at position 10) to the sequences of the four Dengue virus target nucleic acids employed herein, and so represent alternative first-strand primers that can be used to amplify Dengue virus nucleic acids, even when used as the only first-strand primer. The 3' termini of these three primers correspond to the three positions separating the 3' termini of tagged promoter-primers that included the target-hybridizing sequences of SEQ ID NO: 4 (i.e., conforming to SEQ ID NO: 42) and SEQ ID NO: 11 (i.e., conforming to SEQ ID NO: 10), both of which gave excellent results in the amplification assay. Certain first-strand promoter-primers having 8 or more bases deleted from the 3'-end of the target-hybridizing sequence of SEQ ID NO: 2 gave lower reactivity levels, and so are less preferred for use in the most highly sensitive assays for amplifying and detecting Dengue virus nucleic acids. Thus, preferred first-strand primers can include target-hybridizing sequences selected from the group identified by SEQ ID NO: 1 (e.g., SEQ ID NO: 2), SEQ ID NO: 42 (e.g., SEQ ID NO: 4), SEQ ID NO: 43 (e.g., SEQ ID NO: 5), SEQ ID NO: 44 (e.g., SEQ ID NO: 6), SEQ ID NO: 45 (e.g., SEQ ID NO: 7), SEQ ID NO: 10 (e.g., SEQ ID NO: 11), SEQ ID NO: 46 (e.g., SEQ ID NO: 8), and SEQ ID NO: 47 (e.g., SEQ ID NO: 9). Oligonucleotides including these target-hybridizing sequences joined downstream of a phage promoter sequence (e.g., given by SEQ ID NO: 28 or SEQ ID NO: 26) represent highly preferred promoter-primers.

It was concluded that the 3' terminal sequence of the first-strand priming oligonucleotide had a strong effect on assay sensitivity, and that there was some flexibility in pairing of the first-strand priming oligonucleotides with opposite-strand priming oligonucleotides to result in amplicon production when target amounts were very low. Consequently, preferred kits for detecting Dengue virus will include a first-strand priming oligonucleotide, wherein the 3' terminal base sequence of the first-strand priming oligonucleotide is any of those listed in Table 3, with an opposite-strand priming oligonucleotide being optional (e.g., being provided by an end-user of the kit). Of course, preferred second-strand priming oligonucleotides, or opposite-strand priming oligonucleotides, that can hybridize to extension products of the first-strand priming oligonucleotides using one of the four Dengue virus transcripts disclosed herein as a template include at least one of SEQ ID NO:19, SEQ ID NO:13, and SEQ ID NO:16.

While target-hybridizing sequences were essential components of the disclosed first-strand priming oligonucleotides, with upstream promoter sequences and upstream tag sequences being optional for the amplification methods presented herein under Examples 1-3, it was recognized that, in one instance a base contributed by these optional sequences fortuitously was able to hybridize to one of the cloned Dengue virus targets. More specifically, an A residue immediately upstream of the target-hybridizing sequence of each of SEQ ID Nos:1, 10, and 42-47 was complementary to the corresponding position in the model Dengue virus serotype 3 template (i.e., SEQ ID NO:38). Accordingly, priming oligonucleotides having the target-hybridizing sequences presented in Table 3 can be substituted by the priming oligonucleotides presented in Table 4, particularly for amplification of Dengue virus serotype 3. In all cases, position 11 of the sequences in Table 4 is preferably occupied by any of G, T/U, A or C; or more preferably occupied by any of G, T/U or A, or even I (inosine). Again, the target-hybridizing sequences of each of SEQ ID NOs:48-55 can optionally be joined to upstream promoter sequences, and further optionally joined to tag sequences positioned between the given target-hybridizing base sequences and the upstream promoter sequences.

TABLE 4

Target-Hybridizing Sequences for Alternative First-Strand Priming Oligonucleotides

| Sequence | Identifier |
| --- | --- |
| ACGGTTTCTCNCGCGTTTCAGCATATTGA | SEQ ID NO: 48 |
| ACGGTTTCTCNCGCGTTTCAGCATATTG | SEQ ID NO: 49 |

TABLE 4-continued

Target-Hybridizing Sequences for Alternative First-Strand Priming Oligonucleotides

| Sequence | Identifier |
| --- | --- |
| ACGGTTTCTCNCGCGTTTCAGCATATT | SEQ ID NO: 50 |
| ACGGTTTCTCNCGCGTTTCAGCATAT | SEQ ID NO: 51 |
| ACGGTTTCTCNCGCGTTTCAGCATA | SEQ ID NO: 52 |
| ACGGTTTCTCNCGCGTTTCAGCAT | SEQ ID NO: 53 |
| ACGGTTTCTCNCGCGTTTCAGCA | SEQ ID NO: 54 |
| ACGGTTTCTCNCGCGTTTCAGC | SEQ ID NO: 55 |

Example 2 describes procedures that were followed to assess performance of the 5' assay with respect to amplifying and detecting the four Dengue virus serotypes. The use of in vitro transcripts corresponding to the live virus samples of Example 1 permitted highly accurate quantitation of assay sensitivity. Reagents used in the procedure included oligonucleotides having target-hybridizing sequences conforming to the sequences of SEQ ID NO: 1, SEQ ID NO: 10, SEQ ID NO: 13, SEQ ID NO: 16, and SEQ ID NO: 19. Results from the procedure confirmed that the 5' assay detected all four serotypes at levels well below 50 copies/ml, and indeed below 25 copies/ml with sensitivities that advantageously were not statistically different.

Example 2

Quantifying Assay Sensitivity

Oligonucleotides used in the preceding Example for amplifying nucleic acids from live viruses also were used for amplifying and detecting in vitro transcripts containing the amplification target sequences for each of the four Dengue virus serotypes. The procedure further included a target capture step preliminary to amplification and detection. The in vitro transcripts were used at concentrations of 100, 33, 11, 3, 1 and 0 copies/ml (i.e., with 0.5 ml aliquots being used for each assay). Replicates of 152 reactions were carried out for each input copy level. Results comparing the number of positively reactive assays and the number of valid assays are presented in Table 5. Regression analysis using the Probit function in SAS® System software (version 9.1.3) (Cary, N.C.) was used to calculate the 95% detection levels (i.e., target concentration required for 95% probability of detection). Those results are presented in Table 6.

TABLE 5

Combined Data for Dengue Virus Reactivity at Various Copy Levels

| Transcript (copies/ml) | Dengue-1 | | Dengue-2 | | Dengue-3 | | Dengue-4 | |
| --- | --- | --- | --- | --- | --- | --- | --- | --- |
| | No. Valid | No. Reactive | No. Valid | No. Reactive | No. Valid | No. Reactive | No. Valid | No. Reactive |
| 100 | 152 | 152 | 152 | 152 | 151 | 151 | 152 | 152 |
| 33 | 152 | 152 | 152 | 151 | 152 | 152 | 152 | 152 |
| 11 | 152 | 141 | 152 | 134 | 151 | 142 | 152 | 136 |
| 3 | 151 | 75 | 152 | 71 | 152 | 82 | 152 | 74 |
| 1 | 152 | 42 | 152 | 31 | 152 | 38 | 152 | 33 |
| 0 | 152 | 0 | 152 | 0 | 152 | 0 | 152 | 0 |

TABLE 6

Quantifying Sensitivity of the 5' Region Assay

| Target | 95% Detection (copies/ml) |
| --- | --- |
| Dengue-1 | 14.9 (11.7-20.4) |
| Dengue-2 | 18.3 (14.4-24.7) |
| Dengue-3 | 13.0 (10.3-17.6) |
| Dengue-4 | 16.4 (13.0-22.2) |

Based on the results presented in Table 6, differences in the analytical sensitivities for each of the four serotypes were determined to be not statistically significant. Thus, the 5' region amplification and detection assay advantageously detected all Dengue virus serotypes at levels below 50 copies/ml, and even in the range of from 10-25 copies/ml with substantially similar sensitivities.

The combination of results presented in Tables 1 and 3 allowed calculation of a conversion factor that permitted assignment of target copy level concentrations to the live virus samples. Conversion factors were determined by correlating the 95% detection probability levels for live virus and transcript using the 5' region assay. Table 7 presents the calculated copy level values for 95% detection probability using the 3' region assay. The copy level sensitivities from Table 7 were generally useful for comparing sensitivities of alternate assays disclosed herein.

TABLE 7

Quantifying Sensitivity of the 3' Region Assay

| Target | 95% Detection (copies/ml) |
| --- | --- |
| Dengue-1 | 97.1 |
| Dengue-2 | 56.2 |
| Dengue-3 | 57.5 |
| Dengue-4 | 26.9 |

In addition to the assay described in the preceding Examples, there also was created an assay that shared certain of the oligonucleotides used for amplification and detection. More specifically, one of the T7 promoter-primers, two of the non-T7 primers, and the probe described in the formulation of the preceding Example were used in the assay formulation described below.

The following Example describes procedures that demonstrated an alternate 5' region assay for detecting all Dengue virus serotypes. The procedure described did not include the internal amplification and detection control, and so it was not possible to verify the validity of trials that were non-reactive with the hybridization probes. Reagents used in the procedure included oligonucleotides having target-hybridizing sequences conforming to the sequences of SEQ ID NO: 1, SEQ ID NO: 13, and SEQ ID NO: 19.

Example 3

Amplification of Dengue Virus Nucleic Acids

Amplification reactions were performed using oligonucleotides targeting the 5' region of the Dengue virus genome in a sequence having only moderate sequence conservation. The target capture oligonucleotide used for purifying nucleic acids preliminary to the amplification and detection reactions had the target-complementary sequence of SEQ ID NO: 30 joined at it's 3'-end to a sequence of three T residues followed by 30 A residues (i.e., SEQ ID NO: 33). Oligonucleotide primers used in the 5' region assay included the Dengue virus target-hybridizing sequences of SEQ ID NO: 2 (i.e., conforming to SEQ ID NO: 1) joined downstream of the optional tagged promoter sequence of SEQ ID NO: 26 (i.e., the full sequence being given by SEQ ID NO: 3), together with SEQ ID NO: 14 and SEQ ID NO: 15 (i.e., the latter two primers conforming to SEQ ID NO: 13). Detection of amplification products was by hybridization of a mixture of labeled probes having the sequences of SEQ ID NO: 22 and SEQ ID NO: 23 (i.e., both conforming to SEQ ID NO: 19). Notably, amplification products were detected with good results using these probes individually. Thus, use of the probe combination is regarded as redundant and optional, with compositions and methods employing the individual probes each representing separate preferred embodiments.

Amplification reactions were carried out over the course of two days using replicates of 10 for tests using 100, 33 and 11 copies/ml of the different in vitro transcripts. All of 10 negative control reactions that did not include any Dengue virus nucleic acid were non-reactive in the assay, as expected. All of 10 positive control reactions that included a mixture of in vitro transcripts at 300 copies/ml for each of the four Dengue virus serotypes were positively reactive, also as expected. Amplification and detection reactions were as described in the previous Example, except for the omission of the internal control template and probe. Determination of the input copy level sensitivity for each of the Dengue virus serotypes was according to the regression analysis described in the previous Example. A single, aberrant data point for the amplification reaction conducted using the Dengue-3 transcript at 33 copies/ml was excluded from the calculations. Results from the procedure are summarized in the following table which, for completeness, presents both the 95% and 90% detection level probabilities.

TABLE 8

Quantifying Sensitivity of the 5' Region Assay

| Target | 95% Detection (copies/ml) | 90% Detection (copies/ml) |
|---|---|---|
| Dengue-1 | 13.3 | 12.5 |
| Dengue-2 | 13.8 | 13.0 |
| Dengue-3 | 12.7 | 11.9 |
| Dengue-4 | 11.0 | 11.0 |

The results presented in Table 8 indicated that the assay was significantly more sensitive than the 3' assay (see Table 7 for comparison), and advantageously exhibited a somewhat more uniform range for the detection of the different serotypes. Relative to the comparative 3' region assay, the 5' region assay described in this Example was more sensitive at detecting Dengue virus serotypes 1-4 at the 95% detection level by 7.3 fold, 4.1 fold, 4.5 fold, and 2.4 fold, respectively. Whereas the highest and lowest sensitivities for the comparative assay differed by 3.6 fold, the highest and lowest sensitivities for the 5' region assay described in this Example differed by only 1.25 fold. This indicated that the invented 5' region assay was highly sensitive, and was able to detect all four Dengue virus serotypes substantially equivalently.

Another embodiment of the invention employed only two opposite-strand primers for amplifying the four Dengue virus serotypes, and a single probe for detecting the different amplification products. As in the other reactions disclosed herein, no ligation step or ligase enzyme was employed to achieve the amplification. Nucleic acid polymerases served to amplify a relatively short region of the Dengue virus analyte nucleic acid. A hybridization probe detected Dengue-specific amplification products. As illustrated, the probe and primer oligonucleotides preferably are physically separate, meaning that they can have independent backbones that are not contiguous. In Example 4, the first-strand primer (i.e., the tagged promoter oligonucleotide) hybridized to a Dengue virus nucleic acid and was carried through a target capture step into the amplification reaction mixture. This primer, which is exhausted early in the amplification reaction, was known to be essential for beginning the amplification reaction. Omitting this primer fails to result in meaningful amplification of specific Dengue virus sequences. The hybridization probe used for detecting amplification products had a sequence that was fully complementary over its length to the Dengue virus target-hybridizing sequence of the tagged promoter oligonucleotide. The general amplification mechanism employed in this Example is taught by Becker et al., in commonly owned U.S. patent application Ser. No. 11/810,834, the disclosure of which is incorporated by reference.

Example 4 describes procedures for amplifying and detecting nucleic acids of Dengue virus serotypes 1-4, where only two spaced-apart Dengue virus sequences were required for specific amplification and detection of the analyte nucleic acids. One primer in the reaction mixture was used for creating an amplifiable template that was absent from the biological sample to be tested for the presence of Dengue virus. The hybridization probe used for detection of amplification products was complementary over its length to a sequence contained within the target-hybridizing sequence of the Dengue-specific tagged promoter oligonucleotide. Reagents used in the procedure for amplifying Dengue virus nucleic acids included oligonucleotide primers having target-hybridizing sequences conforming to SEQ ID NO: 1 and SEQ ID NO: 19.

The oligonucleotide probe was complementary over its length to the target-hybridizing sequence of the first of these primers.

Example 4

Amplification and Detection of Dengue Virus Serotypes 1-4 Using a Universal Amplification Format Calibration, negative control, and analyte nucleic acid amplification reactions were prepared and run in parallel. Each of a number of disposable plastic tubes for performing Dengue virus analyte nucleic acid amplification reactions received 400 µl of a target capture reagent (TCR), and 500 µl of a buffered carrier solution containing an in vitro transcript for one of Dengue virus serotypes 1-4. Replicates of 5 tubes were prepared for each target level (11, 33, 100, and 300 copies/ml) for each of the four Dengue virus serotypes. Replicates of 10 tubes were prepared for negative control ("Neg. Control") reactions that omitted all Dengue virus nucleic acids. Results from the negative control trials served as controls for all Dengue virus analyte nucleic acid trials. Replicates of 3 tubes prepared for use as negative calibrator ("Neg. Calibrator.") trials each received the TCR aliquot and 500 µl of the buffered carrier solution that contained no Dengue virus template nucleic acids. Replicates of 3 tubes prepared for use as positive calibrator ("Pos. Calibrator") trials each received the TCR aliquot and 500 µl of buffered carrier solution containing 300 copies/ml of Dengue virus serotype-4 in vitro transcript. Both the negative and positive calibrator trials served to establish cutoff values subsequently used for determining reactivity (i.e., the presence of a Dengue virus analyte) in the samples containing Dengue virus analyte nucleic acids. All amplification reactions included an internal control to validate the integrity of amplification reactions yielding Dengue virus non-reactive results. Thus, each target-capture reaction included 300 copies of an internal control in vitro transcript of SEQ ID NO: 41. This internal control was essentially identical to the Dengue virus serotype-1 transcript, except that nucleotide positions 150-173 of SEQ ID NO: 41 represented an HIV-1 sequence (i.e., a sequence absent from Dengue virus nucleic acid) that distinguished authentic Dengue virus targets from the internal control. As a result of the modification, the tagged promoter oligonucleotide that hybridized to each of the four Dengue virus serotypes during the target-capture step was incapable of hybridizing to internal control template. The internal control template was hybridized by a separate internal control specific tagged promoter oligonucleotide that was incapable of hybridizing to the nucleic acids of Dengue virus serotypes 1-4. The TCR included magnetic particles (Seradyn, Inc.; Indianapolis, Ind.) displaying surface oligo(dT)$_{14}$; a target-capture oligonucleotide having a stretch of poly(dA) joined to a sequence complementary to Dengue virus nucleic acid; and separate tagged promoter oligonucleotides specific for Dengue virus analyte and internal control nucleic acids. The tagged promoter oligonucleotide specific for Dengue virus nucleic acid was a promoter-primer having a target-hybridizing sequence of SEQ ID NO: 2 joined downstream of the optional tagged promoter sequence of SEQ ID NO: 26 (i.e., the full sequence being given by SEQ ID NO: 3). The target-capture oligonucleotide had the target-hybridizing sequence of SEQ ID NO: 30. The tagged promoter oligonucleotide specific for internal control nucleic acid included the target-hybridizing sequence of SEQ ID NO: 34 downstream of the optional tagged promoter sequence of SEQ ID NO: 26 (i.e., the full sequence being given by SEQ ID NO: 35). These components of the TCR were dissolved or dispersed in a target capture solution that included 790 mM HEPES (pH 7.3-7.5), 680 mM LiOH, 230 mM succinic acid (free acid), and 10% lithium lauryl sulfate. In this procedure the target capture solution also served as the buffered carrier solution for all of the in vitro transcripts. As a result, the final buffer and salt conditions in the hybridization reaction mixture were essentially identical to the those of the target capture solution. Mixtures were incubated 20 minutes at 60° C. to facilitate hybridization of the target-capture oligonucleotide and tagged promoter oligonucleotides to the Dengue virus analyte nucleic acids and internal control. Mixtures were brought to room temperature following the hybridization step, and excess tagged promoter oligonucleotides that were not hybridized to Dengue virus nucleic acids or internal control were removed from the system. This was accomplished by applying a magnetic field to the sample tubes, and removing the solution phase by aspiration. This separated unhybridized tagged promoter oligonucleotides from magnetic particles complexed with target capture oligonucleotide bound to Dengue virus nucleic acid, and further complexed with tagged promoter oligonucleotide bound to Dengue virus nucleic acid. Similarly, the separation step separated unhybridized tagged promoter oligonucleotides from magnetic particles complexed with target capture oligonucleotide bound to internal control nucleic acid, and further complexed with tagged promoter oligonucleotide bound to internal control nucleic acid. Magnetic bead complexes remaining in the tubes were further purified by washing with a solution that included 10 mM HEPES, 6.5 mM NaOH, 1 mM EDTA, 0.3% (v/v) ethyl alcohol, 0.02% (w/v) methyl paraben, 0.01% propyl paraben, 150 mM NaCl, and 0.1% (w/v) sodium dodecyl sulfate, pH 7.5, and removing the liquid phase containing and materials not immobilized to the magnetic beads. The complex comprising the Dengue virus target RNA and tagged promoter oligonucleotide remained stable in the wash solution. Likewise, the complex comprising the internal control RNA and tagged promoter oligonucleotide remained stable in the wash solution.

Amplification reactions were prepared by combining the purified magnetic bead complexes from individual tubes with 75 µl aliquots of an amplification reagent and 200 µl of an inert oil overlay to control evaporation. The amplification reagent included 11.6 mM Trizma® base buffer, 15 mM Trizma® HCl buffer, 25 mM MgCl$_2$, 23.3 mM KCl, 3.33% (v/v) glycerol, 0.05 mM zinc acetate, 0.76 mM dATP, 0.76 mM dCTP, 0.76 mM dGTP, 0.76 mM dTTP, 0.02% (v/v) ProClin 300 Preservative (Supelco; Bellefonte, Pa.), 6.0 mM ATP, 6.0 mM CTP, 6.0 mM GTP, and 6.0 mM UTP (pH 7.81-8.0 at 22° C.). The amplification reagent further included primers having the sequences of SEQ ID NO: 26 and SEQ ID NO: 21 (i.e., conforming to SEQ ID NO: 19). The primer of SEQ ID NO: 26 served as a universal promoter-primer that was not complementary to any Dengue virus analyte nucleic acid. Instead, this primer was useful for amplifying an artificial template synthesized in the reaction mixture after amplification had commenced. Contents of the tubes were mixed gently and then equilibrated to 42° C. Next, reaction mixtures received 25 µl aliquots of an enzyme reagent, and were again mixed gently and incubated at 42° C. for an additional 60 minutes. The enzyme reagent included 70 mM N-acetyl-L-cysteine, 10% (v/v) TRITON® X-102 detergent, 16 mM HEPES, 3 mM EDTA, 0.05% (w/v) sodium azide, 20 mM Trizma® base buffer, 50 mM KCl$_2$, 20% (v/v) glycerol, 165.6 mM trehalose, pH 7, and containing 224 U/µL Moloney murine leukemia virus ("MMLV") reverse transcriptase and 140 U/µL T7 RNA polymerase, where one unit of activity is defined as the synthesis and release of 5.75 fmol cDNA in 15 minutes at 37° C. for MMLV reverse transcriptase, and the production of 5.0 fmol RNA transcript in 20 minutes at 37° C. for T7 RNA polymerase.

At the conclusion of the 60 minute incubation period, the amplification reaction mixtures were subjected to hybridization assays using an oligonucleotide probe prepared using 2'-Ome RNA nucleotide analogs. The Dengue virus analyte probe was labeled with acridinium ester according to procedures that will be familiar to those having an ordinary level of skill in the art. The detectable label was joined to the oligonucleotide structure by an internally disposed non-nucleotide linker according to procedures described in U.S. Pat. Nos. 5,585,481 and 5,639,604, the disclosures of these patents are incorporated by reference. Hybridization reactions were carried out by combining the 100 µl amplification reaction volumes with 100 µl of a buffered probe reagent that included an oligonucleotide probe having the sequence of SEQ ID NO: 25 for detection of Dengue virus amplification products, and an oligonucleotide probe having the sequence of SEQ ID NO: 24 for detection of internal control amplification products. Hybridization reactions were incubated for 15 minutes at 62° C. Conditions to promote the hybridization reactions were provided by a solution containing 75 mM succinic acid, 3.5% w/v lithium lauryl sulfate, 75 mM lithium hydroxide, 15 mM aldrithiol-2, 1,000 mM lithium chloride, 1 mM EDTA, 3% v/v ethanol, and adjusted to pH 4.2. The detectable label used on the internal control probe was kinetically distinguishable from the label on the authentic Dengue virus probe using procedures familiar to those having an ordinary level of skill in the art. The oligonucleotide probe for detecting Dengue virus amplification products was fully complementary over its length to the Dengue virus target-hybridizing sequence of the tagged promoter oligonucleotide that had been used for performing the amplification reaction Likewise, oligonucleotide probe for detecting internal control amplification products was fully complementary over its length to the target-hybridizing portion of the internal control-specific tagged promoter oligonucleotide that had been used for performing the amplification reaction. After mixing, tubes were incubated for 15 minutes at 62° C. to promote hybridization of oligonucleotide probes to amplification products. Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label linked to unhybridized probe, and cooled briefly to 4° C. prior to reading the hybridization signal. Chemiluminescence due to hybridized probe in each sample was assayed using commercially available instrumentation (Gen-Probe Incorporated; San Diego, Calif.) configured for injection of 1 mM nitric acid and 0.1% (v/v) hydrogen peroxide, followed by injection of a solution containing 1 N sodium hydroxide. Results for the chemiluminescent reactions were measured in relative light units (RLU).

Results of the amplification and detection reactions, presented in Table 9, were processed using the internal control to assess integrity of the procedures (e.g., to validate any reactions that yielded Dengue virus non-reactivity), and a signal-to-cutoff analysis for determining reactivity. The analyte cutoff was established by adding the average of the negative calibrator signal and 3% of the average of the positive calibrator signal to yield a value of 41,077 RLU. The internal control cutoff was established by dividing in half the average of the internal control signal for the negative calibrator. If any trial that was non-reactive for Dengue virus had an internal control ("IC") signal (i.e., measured in RLU) that was less than or equal to the internal control cutoff, then the reaction was declared invalid. The internal control cutoff value was established to be 92,972 RLU. The average analyte signal values (i.e., "Avg Analyte RLU") listed in the table represent the average of all valid runs at a given level of target nucleic acid (i.e., not only reactives). Reactivity for the four Dengue virus serotypes is listed in the table by indicating both the number of reactive samples and the number of trials carried out at that input target level. Reactivity of trials conducted using the negative and positive calibrators is not presented in the table because those trials were used for setting reactivity criteria. Dengue virus analyte reactivity was judged using a signal-to-cutoff (i.e., S/CO) value. This was done by dividing the analyte signal value (determined for each trial) by the above-described analyte cutoff value. Any S/CO result greater than or equal to 1 was taken as an indication of positive reactivity. Negative control amplification reactions ("Neg. Control" in the table) were carried out in the absence of added Dengue virus template nucleic acid. While similar in constitution to the "Neg. Calibrator" trials in their reaction mixture constitution, results from the negative control reactions were not used for establishing cutoff values. All reactions carried out in the procedure met the internal control cutoff threshold, thereby confirming valid results for each trial. Notably, there were no false-positive results in the procedure.

TABLE 9

Amplification and Detection of Dengue Virus Nucleic Acids

| Target | Target Copy Level (c/ml) | Avg Analyte Signal (RLU) | Avg. S/CO for Reactive Trials | Reactivity (# reactive/ # trials) | Avg IC Signal (RLU) |
|---|---|---|---|---|---|
| Neg. Calibrator | 0 | 3,679 | — | — | 185,944 |
| Pos. Calibrator | 300 | 1,246,586 | 30.3 | — | 189,541 |
| Neg. Control | 0 | 6,858 | — | 0/10 | 178,368 |
| Dengue-1 | 11 | 162,342 | 6.2 | 3/5 | 175,682 |
|  | 33 | 186,318 | 4.5 | 5/5 | 168,339 |
|  | 100 | 513,305 | 12.5 | 5/5 | 182,717 |
|  | 300 | 998,380 | 24.3 | 5/5 | 211,660 |
| Dengue-2 | 11 | 682,018 | 16.6 | 5/5 | 187,133 |
|  | 33 | 761,724 | 23.1 | 4/5 | 201,803 |
|  | 100 | 1,321,165 | 32.2 | 5/5 | 199,298 |
|  | 300 | 1,395,627 | 34.0 | 5/5 | 238,835 |
| Dengue-3 | 11 | 106,364 | 3.9 | 3/5 | 153,989 |
|  | 33 | 120,062 | 2.9 | 5/5 | 168,808 |
|  | 100 | 421,807 | 10.3 | 5/5 | 156,063 |
|  | 300 | 527,746 | 15.4 | 5/5 | 181,978 |
| Dengue-4 | 11 | 222,559 | 6.6 | 4/5 | 160,116 |
|  | 33 | 659,640 | 16.1 | 5/5 | 168,416 |
|  | 100 | 1,081,714 | 26.3 | 5/5 | 172,313 |
|  | 300 | 1,236,345 | 30.1 | 5/5 | 211,239 |

Regression analysis using the Probit function in SAS® System software (version 9.1.3) (Cary, N.Y.) was applied to the results in Table 9 to calculate 95% and 90% detection levels (i.e., target concentrations required for 95% and 90% probabilities of detection, respectively) for each serotype. This analysis required as inputs the target copy level (i.e., measured in copies/ml) and the fractional reactivity. The analysis outputted the target copy level required to achieve a predetermined detection level (i.e., chosen to be 95% and 90% probability of detection). Results of the analysis are presented in Table 10.

TABLE 10

Amplification and Detection of Dengue Virus Serotypes 1-4 With Equivalent Sensitivity

| Target | 95% Detection Level (copies/ml) | 90% Detection Level (copies/ml) |
| --- | --- | --- |
| Dengue-1 | 13.8 | 13.0 |
| Dengue-2 | 44.1 | 8.2 |
| Dengue-3 | 13.8 | 13.0 |
| Dengue-4 | 12.7 | 11.9 |

The results presented in Table 9 indicated that the 95% detection level for all four Dengue virus serotypes was in the range of from 12-50 copies/ml. The 90% detection level for all four Dengue virus serotypes was advantageously in the range of from 8-50 copies/ml, and even in the range of from 8-15 copies/ml. These ranges confirmed that all four Dengue virus serotypes were detected with substantially similar sensitivity.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of determining whether a test sample contains Dengue virus, said method comprising the steps of:
    (a) obtaining nucleic acids from the test sample;
    (b) performing an in vitro nucleic acid amplification reaction using the nucleic acids obtained in step (a) as templates for amplification with a set of primers, whereby there is produced an amplification product if said test sample comprised nucleic acids of any of Dengue virus serotypes 1-4,
    wherein the base sequence of a first member of said set of primers consists of a target-hybridizing sequence of SEQ ID NO:2, optionally joined to an upstream promoter sequence, and further optionally joined to an upstream tag sequence, wherein neither said upstream promoter sequence nor said upstream tag sequence can hybridize to the nucleic acid of any of Dengue virus serotypes 1-4 and participate in said in vitro nucleic acid amplification reaction in the absence of joining to said target-hybridizing sequence, and
    wherein the base sequence of a second member of said set of primers consists of SEQ ID NO:14; and
    (c) detecting, with a first detectably labeled hybridization probe, any of said amplification product that may have been produced in the in vitro nucleic acid amplification reaction, wherein the base sequence of said first detectably labeled hybridization probe is SEQ ID NO:22 or the complement thereof, allowing for substitution of RNA and DNA equivalent bases,
    whereby detecting said amplification product determines that the test sample contains at least one of Dengue virus serotypes 1-4, and
    whereby failing to detect said amplification product determines that the test sample does not contain Dengue virus.

2. The method of claim 1, wherein obtaining step (a) comprises capturing nucleic acids from the test sample onto a solid support, and then isolating the solid support.

3. The method of claim 1, wherein the in vitro nucleic acid amplification reaction in performing step (b) is an isothermal in vitro nucleic acid amplification reaction.

4. The method of claim 1, wherein detecting step (c) comprises detecting by a procedure selected from the group consisting of luminometry and fluorometry.

5. The method of claim 1, wherein detecting step (c) comprises detecting a chemiluminescent signal by luminometry.

6. The method of claim 1, wherein the base sequence of said first member of said set of primers in performing step (b) consists of said target-hybridizing sequence of SEQ ID NO:2 joined to said upstream promoter sequence.

7. The method of claim 1, wherein detecting step (c) comprises measuring an optical signal produced by said detectably labeled hybridization probe, and then comparing the measured optical signal to a cutoff value.

8. The method of claim 1, wherein the test sample is selected from the group consisting of blood, blood products, and serum.

9. The method of claim 6, wherein said set of primers further comprises a third member, and wherein the base sequence of said third member of said set of primers is SEQ ID NO:15.

10. The method of claim 1, wherein said set of primers further comprises a third member, and wherein the base sequence of said third member of said set of primers is SEQ ID NO:15.

11. The method of claim 6, further comprising a second detectably labeled hybridization probe, wherein the base sequence of said second detectably labeled hybridization probe is SEQ ID NO:23 or the complement thereof, allowing for substitution of RNA and DNA equivalent bases.

12. The method of claim 1, further comprising a second detectably labeled hybridization probe, wherein the base sequence of said second detectably labeled hybridization probe is SEQ ID NO:23 or the complement thereof, allowing for substitution of RNA and DNA equivalent bases.

* * * * *